United States Patent [19]
Barry et al.

[11] Patent Number: 5,750,876
[45] Date of Patent: May 12, 1998

[54] ISOAMYLASE GENE, COMPOSITIONS CONTAINING IT, AND METHODS OF USING ISOAMYLASES

[75] Inventors: Gerard Francis Barry, St. Louis; Ganesh Murthy Kishore, Chesterfield; Bradley Martin Krohn, St. Louis, all of Mo.

[73] Assignee: Monsanto Company, St. Louis, Mo.

[21] Appl. No.: 476,519

[22] Filed: Jun. 7, 1995

Related U.S. Application Data

[63] Continuation-in-part of Ser. No. 281,902, Jul. 28, 1994, abandoned.

[51] Int. Cl.$^6$ .......................... A01H 5/00; C12N 15/31; C12N 15/54; C12N 15/82; C12P 19/04
[52] U.S. Cl. .......................... 800/205; 800/DIG. 42; 800/DIG. 55; 800/DIG. 56; 800/DIG. 57; 800/DIG. 58; 435/69.1; 435/69.7; 435/69.8; 435/70.1; 435/101; 435/172.3; 435/98; 435/194; 435/252.31; 435/252.33; 435/254.2; 435/412; 435/417; 435/419; 536/23.2; 536/23.4; 536/23.7
[58] Field of Search .......................... 536/23.2, 23.7, 536/23.4; 435/69.1, 69.7, 69.8, 70.1, 101, 172.3, 240.4, 252.31, 252.33, 254.2, 98, 194, 419, 412, 417; 800/205, DIG. 42, DIG. 55, DIG. 56, DIG. 57, DIG. 58

[56] References Cited

U.S. PATENT DOCUMENTS 5,300,145  4/1994  Fergason et al. .......................... 106/213

FOREIGN PATENT DOCUMENTS

WO90/12876  11/1990  WIPO .......................... C12N 15/56
WO91/19806  12/1991  WIPO .......................... C12N 15/82
WO92/05259  4/1992  WIPO .......................... C12N 15/56

OTHER PUBLICATIONS

Sato and Park (1980) Starch 32:Nr. 4,S.132–136 | Purification and Characterization of Extracellular Isoamylase from Flavobacterium sp.

Amemura et al. (1988) J. Biol. Chem. 263(19):9271–9275.

"Approaches to influence starch quantity and starch quality in transgenic plants" Müller–Röber B. and Kossman J., Plant, Cell and Environment, vol. 17, No. 5, 1994, pp. 601–613.

"Progress in the genetic manipulation of crops aimed at changing starch accumulation", Sivak M.N. and Preiss J., Databse Scisearch Institute for Scientific Information, Philadelphia, PA Genuine Article #:RU657, see abstract & J. Env. Polymer Degradation, vol. 3, No. 3, Jul. 1995, pp. 145–152.

Odibo, F.J.C. et al., *World J. Microbiol. Biotechnol.*, 8:102–105 (1992).

*Primary Examiner*—David T. Fox
*Attorney, Agent, or Firm*—Grace L. Bonner; Arnold, White & Durkee

[57] ABSTRACT

A method of producing plant products containing modified starch content, including higher ratios of amylose to amylopectin, increase in intermediate material, or amylopectin having fewer branches or altered branching pattern. Also provided are DNA constructs and transformed plant cells useful in that method. The preferred method uses isoamylase from a Flavobacterium sp., more preferably in combination with a gene encoding ADPglucose pyrophosphorylase. Also disclosed are the gene from Flavobacterium sp. and transformed bacterial and plant cells containing a derivative thereof.

28 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2334 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATGGACCCAC  ACGCCCCGCA  GCGGCAACGA  AGCGGGCAGC  GCTTGCGCGC  CCTCGCCCTG     60

GCCGCGCTGG  CCTGCGCGCT  GAGCCCGGCC  CACGCCGCCA  TCGATGCGCA  GCAGCTCGGC    120

GCGCGCTACG  ACGCCGCCCA  GGCCAACCTC  GCGTTCCGGG  TCTATTCCTC  GCGCGCGACC    180

CGCGTCGAGG  TGTTCCTGTA  CAAGAACCCG  ACCGGCTCGC  AGGAAGTCGC  GCGGCTGGCG    240

CTGAGCAAGG  ACCCGGCGAC  CCAGGTGTGG  TCGCTGTCGC  TGCCGACCAG  CACGATCAAG    300

AACACCTACG  GCATCACCGG  CGCCGTCTAC  TACGGTTACC  GCGCCTGGGG  CCCGAACTGG    360

CCCTACGATG  CGGCCTGGAC  CAAGGGCAGC  GCCACCGGCT  TCGTCAGCGA  CGTCGACAAC    420

GCCGGCAACC  GTTTCAATCC  GAACAAGCTG  CTGCTCGACC  CCTACGCGCG  CGAGATCAGC    480
```

| | | | | | |
|---|---|---|---|---|---|
| CAGGACCCGA | ACACCGCGAC | CTGCGCCGAC | GGCACCATCT | ACGCCACCGG | CGCCGCGCAC | 540 |
| CGCAACAAGG | ACAGCGGCCT | GTGCGCGAGC | AAGGGCATCG | CGCTGGCCGC | GGACGCGACC | 600 |
| TCGGTCGGCA | GCAAGCCGAC | CCGCGCGCTC | AAGGACGAGG | TGATCTACGA | AGTGCACGTG | 660 |
| CGCGGCCTGA | CCCGCAACGA | CGACAGCGTG | CCCGCGGCCG | AACGCGGCAC | CTACAAGGGC | 720 |
| GCCGCGCGCA | AGGCCGCCGC | GTTGGCCGCG | CTCGGCGTCA | CCGCGGTCGA | GTTCCTGCCG | 780 |
| GTGCAGGAAA | CCCAGAACGA | CCAGAACGAT | GTCGATCCCA | ATTCCACCGC | GGGCGACAAC | 840 |
| TACTGGGGCT | ACATGACCCT | CAACTACTTC | GCCCCGGACC | GCCGCTACGC | CTACGACAAG | 900 |
| TCGGCCGGCG | GGCCGACCCG | CGAATGGAAG | GCGATGGTCA | AGGCCTTCCA | CGACGCCGGC | 960 |
| ATCAAGGTCT | ACATCGACGT | GGTCTACAAC | CACACCGGCG | AAGGCGGCCC | GTGGAGCGGC | 1020 |
| ACCGACGGGC | TCAGCGTCTA | CAACCTGCTC | TCGTTCCGCG | GCCTCGACAA | CCCGGCCTAC | 1080 |
| TACTCGCTGA | GCAGCGATTA | CAAGTATCCG | TGGACAACA | CCGGCGTCGG | CGGCAACTAC | 1140 |
| AACACCCGCC | ATCCCATCGC | CCAGAACCTG | ATCGTCGACT | CGCTGGCGTA | CTGGCGCGAC | 1200 |
| GCGCTCGGCG | TAGACGGTTT | CCGCTTCGAT | CTGGCCTCGG | TGCTCGGCAA | CAGCTGCCAG | 1260 |
| CACGGCTGCT | TCAACTTCGA | CAAGAACGAC | TCGGGCAACG | CGCTCAACCG | CATCGTCGCC | 1320 |
| GAGCTGCCGC | CGCGCCCGGC | CGCGGGCGGC | GCCGGCGCGG | ACCTGATCGC | CGAACCCTGG | 1380 |
| GCGATCGGCG | GCAACTCCTA | CCAGGTCGGC | GGCTTCCCGG | CCGGCTGGGC | CGAGTGGAAC | 1440 |
| GGCCTCTACC | GCGACGCGCT | GCGCAAGAAG | CAGAACAAGC | TCGGCGTGGA | ACGGTCACC | 1500 |
| CCCGGCACCC | TGGCCACGCG | CTTCGCCGGC | TCCAACGACC | TGTACGGCGA | CGACGGCCGC | 1560 |
| AAGCCGTGGC | ATTCGATCAA | CTTCGTGGTC | GCCCACGACG | GCTTCACCCT | CAACGACCTG | 1620 |
| TACGCCTACA | ACGACAAGCA | GAACAACCAG | CCGTGGCCGT | ACGGGCCGTC | CGACGGCGGC | 1680 |
| GAGGACCACA | ACCTGAGCTG | GAACCAGGGC | GGCATCGTCG | CCGAGCAGCG | CAAGGCCGCG | 1740 |
| CGCACCGGAC | TGGCGTTGCT | GATGCTCAGC | GCCGGCGTGC | CGATGATCAC | CGGCGGCGAC | 1800 |
| GAGGCGCTGC | GCACCCAGTT | CGGCAACAAC | AACACCTACA | ACCTGGATTC | GGCGGCCAAC | 1860 |
| TGGCTGTACT | GGAGCCGCAG | CGCGCTCGAG | GCCGACCACG | AGACCTACAC | CAAGCGCCTG | 1920 |
| ATCGCGTTCC | GCAAGGCGCA | CCCGGCGCTG | CGCCCGGCGA | ACTTCTATTC | GGCCAGCGAC | 1980 |
| ACCAACGGCA | ACGTGATGGA | GCAGTTGCGC | TGGTTCAAGC | CCGACGGCGC | GCAGGCCGAC | 2040 |
| AGCGCCTACT | TCAACGGCGC | CGACAACCAC | GCCCTGGCCT | GGCGCATCGA | CGGCAGCGAG | 2100 |
| TTCGGCGACA | GCGCCAGCGC | GATCTACGTC | GCCTACAACG | GCTGGTCCGG | CGCGGTCGAC | 2160 |
| TTCAAGCTGC | CGTGGCCGGG | CACCGGCAAG | CAGTGGTACC | GGGTCACCGA | TACCGCGACC | 2220 |
| TGGAACGAAG | GCCCCAACGC | GGTGGCGCTG | CCCGGCAGCG | AGACCCTGAT | CGGCGGCGAG | 2280 |
| AACACCGTCT | ACGGCATGCA | GGCGCGCTCG | CTGCTGTTGC | TGATCGCGAA | GTGA | 2334 |

( 2 ) INFORMATION FOR SEQ ID NO:2:

( i ) SEQUENCE CHARACTERISTICS:
        ( A ) LENGTH: 777 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Pro  His  Ala  Pro  Gln  Arg  Gln  Arg  Ser  Gly  Gln  Arg  Leu  Arg
 1                  5                       10                          15

Ala  Leu  Ala  Leu  Ala  Ala  Leu  Ala  Cys  Ala  Leu  Ser  Pro  Ala  His  Ala
             20                      25                      30
```

| Ala | Ile | Asp | Ala | Gln | Gln | Leu | Gly | Ala | Arg | Tyr | Asp | Ala | Ala | Gln | Ala |
|---|---|---|---|---|---|---|---|---|---|---|---|---|---|---|---|
| | | 35 | | | | 40 | | | | | 45 | | | | |
| Asn | Leu | Ala | Phe | Arg | Val | Tyr | Ser | Ser | Arg | Ala | Thr | Arg | Val | Glu | Val |
| | 50 | | | | 55 | | | | | 60 | | | | | |
| Phe | Leu | Tyr | Lys | Asn | Pro | Thr | Gly | Ser | Gln | Glu | Val | Ala | Arg | Leu | Ala |
| 65 | | | | | 70 | | | | 75 | | | | | | 80 |
| Leu | Ser | Lys | Asp | Pro | Ala | Thr | Gln | Val | Trp | Ser | Leu | Ser | Leu | Pro | Thr |
| | | | | 85 | | | | | 90 | | | | | 95 | |
| Ser | Thr | Ile | Lys | Asn | Thr | Tyr | Gly | Ile | Thr | Gly | Ala | Val | Tyr | Tyr | Gly |
| | | | | 100 | | | | 105 | | | | | 110 | | |
| Tyr | Arg | Ala | Trp | Gly | Pro | Asn | Trp | Pro | Tyr | Asp | Ala | Ala | Trp | Thr | Lys |
| | | | 115 | | | | 120 | | | | | 125 | | | |
| Gly | Ser | Ala | Thr | Gly | Phe | Val | Ser | Asp | Val | Asp | Asn | Ala | Gly | Asn | Arg |
| | | 130 | | | | | 135 | | | | | 140 | | | |
| Phe | Asn | Pro | Asn | Lys | Leu | Leu | Leu | Asp | Pro | Tyr | Ala | Arg | Glu | Ile | Ser |
| 145 | | | | | 150 | | | | | 155 | | | | | 160 |
| Gln | Asp | Pro | Asn | Thr | Ala | Thr | Cys | Ala | Asp | Gly | Thr | Ile | Tyr | Ala | Thr |
| | | | | 165 | | | | | 170 | | | | | 175 | |
| Gly | Ala | Ala | His | Arg | Asn | Lys | Asp | Ser | Gly | Leu | Cys | Ala | Ser | Lys | Gly |
| | | | | 180 | | | | | 185 | | | | 190 | | |
| Ile | Ala | Leu | Ala | Ala | Asp | Ala | Thr | Ser | Val | Gly | Ser | Lys | Pro | Thr | Arg |
| | | | 195 | | | | | 200 | | | | | 205 | | |
| Ala | Leu | Lys | Asp | Glu | Val | Ile | Tyr | Glu | Val | His | Val | Arg | Gly | Leu | Thr |
| | | | 210 | | | | | 215 | | | | | 220 | | |
| Arg | Asn | Asp | Asp | Ser | Val | Pro | Ala | Ala | Glu | Arg | Gly | Thr | Tyr | Lys | Gly |
| 225 | | | | | 230 | | | | | 235 | | | | | 240 |
| Ala | Ala | Arg | Lys | Ala | Ala | Ala | Leu | Ala | Ala | Leu | Gly | Val | Thr | Ala | Val |
| | | | | 245 | | | | | 250 | | | | | 255 | |
| Glu | Phe | Leu | Pro | Val | Gln | Glu | Thr | Gln | Asn | Asp | Gln | Asn | Asp | Val | Asp |
| | | | | 260 | | | | | 265 | | | | | 270 | |
| Pro | Asn | Ser | Thr | Ala | Gly | Asp | Asn | Tyr | Trp | Gly | Tyr | Met | Thr | Leu | Asn |
| | | | 275 | | | | | 280 | | | | | 285 | | |
| Tyr | Phe | Ala | Pro | Asp | Arg | Arg | Tyr | Ala | Tyr | Asp | Lys | Ser | Ala | Gly | Gly |
| | | 290 | | | | | 295 | | | | | 300 | | | |
| Pro | Thr | Arg | Glu | Trp | Lys | Ala | Met | Val | Lys | Ala | Phe | His | Asp | Ala | Gly |
| 305 | | | | | 310 | | | | | 315 | | | | | 320 |
| Ile | Lys | Val | Tyr | Ile | Asp | Val | Val | Tyr | Asn | His | Thr | Gly | Glu | Gly | Gly |
| | | | | 325 | | | | | 330 | | | | | 335 | |
| Pro | Trp | Ser | Gly | Thr | Asp | Gly | Leu | Ser | Val | Tyr | Asn | Leu | Leu | Ser | Phe |
| | | | 340 | | | | | 345 | | | | | 350 | | |
| Arg | Gly | Leu | Asp | Asn | Pro | Ala | Tyr | Tyr | Ser | Leu | Ser | Ser | Asp | Tyr | Lys |
| | | | 355 | | | | | 360 | | | | | 365 | | |
| Tyr | Pro | Trp | Asp | Asn | Thr | Gly | Val | Gly | Gly | Asn | Tyr | Asn | Thr | Arg | His |
| | | 370 | | | | | 375 | | | | | 380 | | | |
| Pro | Ile | Ala | Gln | Asn | Leu | Ile | Val | Asp | Ser | Leu | Ala | Tyr | Trp | Arg | Asp |
| 385 | | | | | 390 | | | | | 395 | | | | | 400 |
| Ala | Leu | Gly | Val | Asp | Gly | Phe | Arg | Phe | Asp | Leu | Ala | Ser | Val | Leu | Gly |
| | | | | 405 | | | | | 410 | | | | | 415 | |
| Asn | Ser | Cys | Gln | His | Gly | Cys | Phe | Asn | Phe | Asp | Lys | Asn | Asp | Ser | Gly |
| | | | | 420 | | | | | 425 | | | | | 430 | |
| Asn | Ala | Leu | Asn | Arg | Ile | Val | Ala | Glu | Leu | Pro | Pro | Arg | Pro | Ala | Ala |
| | | | | 435 | | | | | 440 | | | | | 445 | |
| Gly | Gly | Ala | Gly | Ala | Asp | Leu | Ile | Ala | Glu | Pro | Trp | Ala | Ile | Gly | Gly |

|     |     |     |     |     | 450 |     |     |     |     | 455 |     |     |     |     | 460 |     |
| --- | --- | --- | --- | --- | --- | --- | --- | --- | --- | --- | --- | --- | --- | --- | --- | --- |

Asn Ser Tyr Gln Val Gly Gly Phe Pro Ala Gly Trp Ala Glu Trp Asn
465                     470                 475                 480

Gly Leu Tyr Arg Asp Ala Leu Arg Lys Lys Gln Asn Lys Leu Gly Val
                    485                 490                 495

Glu Thr Val Thr Pro Gly Thr Leu Ala Thr Arg Phe Ala Gly Ser Asn
                500                 505                 510

Asp Leu Tyr Gly Asp Asp Gly Arg Lys Pro Trp His Ser Ile Asn Phe
            515                 520                 525

Val Val Ala His Asp Gly Phe Thr Leu Asn Asp Leu Tyr Ala Tyr Asn
530                     535                 540

Asp Lys Gln Asn Asn Gln Pro Trp Pro Tyr Gly Pro Ser Asp Gly Gly
545                 550                 555                 560

Glu Asp His Asn Leu Ser Trp Asn Gln Gly Gly Ile Val Ala Glu Gln
                565                 570                 575

Arg Lys Ala Ala Arg Thr Gly Leu Ala Leu Leu Met Leu Ser Ala Gly
            580                 585                 590

Val Pro Met Ile Thr Gly Gly Asp Glu Ala Leu Arg Thr Gln Phe Gly
        595                 600                 605

Asn Asn Asn Thr Tyr Asn Leu Asp Ser Ala Ala Asn Trp Leu Tyr Trp
610                 615                 620

Ser Arg Ser Ala Leu Glu Ala Asp His Glu Thr Tyr Thr Lys Arg Leu
625                 630                 635                 640

Ile Ala Phe Arg Lys Ala His Pro Ala Leu Arg Pro Ala Asn Phe Tyr
            645                 650                 655

Ser Ala Ser Asp Thr Asn Gly Asn Val Met Glu Gln Leu Arg Trp Phe
            660                 665                 670

Lys Pro Asp Gly Ala Gln Ala Asp Ser Ala Tyr Phe Asn Gly Ala Asp
        675                 680                 685

Asn His Ala Leu Ala Trp Arg Ile Asp Gly Ser Glu Phe Gly Asp Ser
    690                 695                 700

Ala Ser Ala Ile Tyr Val Ala Tyr Asn Gly Trp Ser Gly Ala Val Asp
705                 710                 715                 720

Phe Lys Leu Pro Trp Pro Gly Thr Gly Lys Gln Trp Tyr Arg Val Thr
            725                 730                 735

Asp Thr Ala Thr Trp Asn Glu Gly Pro Asn Ala Val Ala Leu Pro Gly
            740                 745                 750

Ser Glu Thr Leu Ile Gly Gly Glu Asn Thr Val Tyr Gly Met Gln Ala
        755                 760                 765

Arg Ser Leu Leu Leu Leu Ile Ala Lys
770                 775

(2) INFORMATION FOR SEQ ID NO:3:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:3:

Ala Ile Asp Ala Gln Gln Leu Gly Ala Arg Tyr Asp Ala Ala Gln Ala
1               5                   10                  15

Asn Leu Ala Phe Arg Val Tyr Ser Ser Arg Ala Thr Xaa Val Glu Xaa
            20                  25                  30

```
    Phe  Leu  Tyr  Lys  Asn  Pro
              3 5
```

( 2 ) INFORMATION FOR SEQ ID NO:4:

( i ) SEQUENCE CHARACTERISTICS:
        ( A ) LENGTH: 260 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

```
ATCGACGTGG  TCTACAACCA  CACCGGCGAA  GGCGGCCCGT  GGAGCGGCAC  CGACGGGCTC      60

AGCGTCTACA  ACCTGCTCTC  GTTCCGCGGC  CTCGACAACC  CGGCCTACTA  CTCGCTGAGC     120

AGCGATTACA  AGTATCCGTG  GGACAACACC  GGCGTCGGCG  GCAACTACAA  CACCCGCCAT     180

CCCATCGCCC  AGAACCTGAT  CGTCGACTCG  CTGGCGTACT  GGCGCGACGC  GCTCGGCGTA     240

GACGGTTTCC  GCTTCGATCT                                                    260
```

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

```
GGGGCCATGG  CCATCGATGC  GCAGCAGCTC  GGCGCGCGCT  ACGAC                      45
```

( 2 ) INFORMATION FOR SEQ ID NO:6:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

```
CCCCGAATTC  GAGCTCTTAT  CACTTCGCGA  TCAGCAACAG  CAGCGA                     46
```

( 2 ) INFORMATION FOR SEQ ID NO:7:

( i ) SEQUENCE CHARACTERISTICS:
        ( A ) LENGTH: 355 base pairs
        ( B ) TYPE: nucleic acid
        ( C ) STRANDEDNESS: double
        ( D ) TOPOLOGY: linear ( i i ) MOLECULE TYPE: DNA (genomic)

( x ) PUBLICATION INFORMATION:
        ( H ) DOCUMENT NUMBER: WO 91/19806
        ( I ) FILING DATE: 07-JUN-1991
        ( J ) PUBLICATION DATE: 26-DEC- 1991
        ( K ) RELEVANT RESIDUES IN SEQ ID NO:7: FROM 1 TO 355

( x i ) SEQUENCE DESCRIPTION: SEQ ID NO:7:

```
AAGCTTGTTC  TCATTGTTGT  TATCATTATA  TATAGATGAC  CAAAGCACTA  GACCAAACCT      60

CAGTCACACA  AAGAGTAAAG  AAGAACAATG  GCTTCCTCTA  TGCTCTCTTC  CGCTACTATG     120

GTTGCCTCTC  CGGCTCAGGC  CACTATGGTC  GCTCCTTTCA  ACGGACTTAA  GTCCTCCGCT     180
```

```
GCCTTCCCAG CCACCCGCAA GGCTAACAAC GACATTACTT CCATCACAAG CAACGGCGGA         240

AGAGTTAACT GCATGCAGGT GTGGCCTCCG ATTGGAAAGA AGAAGTTTGA GACTCTCTCT         300

TACCTTCCTG ACCTTACCGA TTCCGGTGGT CGCGTCAACT GCATGCAGGC CATGG             355
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Asp Val Val Tyr Asn His
 1               5
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Gly Phe Arg Phe Asp Leu Ala Ser Val
 1               5
```

( 2 ) INFORMATION FOR SEQ ID NO:10:

( i ) SEQUENCE CHARACTERISTICS:
        ( A ) LENGTH: 2244 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2241

( x i ) SEQUENCE DESCRIPTION: SEQ ID NO:10:

```
ATG GCC ATC GAT GCG CAG CAG CTC GGC GCG CGC TAC GAC GCC GCC CAG          48
Met Ala Ile Asp Ala Gln Gln Leu Gly Ala Arg Tyr Asp Ala Ala Gln
 1               5                  10                  15

GCC AAC CTC GCG TTC CGG GTC TAT TCC TCG CGC GCG ACC CGC GTC GAG          96
Ala Asn Leu Ala Phe Arg Val Tyr Ser Ser Arg Ala Thr Arg Val Glu
                20                  25                  30

GTG TTC CTG TAC AAG AAC CCG ACC GGC TCG CAG GAA GTC GCG CGG CTG         144
Val Phe Leu Tyr Lys Asn Pro Thr Gly Ser Gln Glu Val Ala Arg Leu
            35                  40                  45

GCG CTG AGC AAG GAC CCG GCG ACC CAG GTG TGG TCG CTG TCG CTG CCG         192
Ala Leu Ser Lys Asp Pro Ala Thr Gln Val Trp Ser Leu Ser Leu Pro
        50                  55                  60

ACC AGC ACG ATC AAG AAC ACC TAC GGC ATC ACC GGC GCC GTC TAC TAC         240
Thr Ser Thr Ile Lys Asn Thr Tyr Gly Ile Thr Gly Ala Val Tyr Tyr
 65                  70                  75                  80

GGT TAC CGC GCC TGG GGC CCG AAC TGG CCC TAC GAT GCG GCC TGG ACC         288
Gly Tyr Arg Ala Trp Gly Pro Asn Trp Pro Tyr Asp Ala Ala Trp Thr
                 85                  90                  95

AAG GGC AGC GCC ACC GGC TTC GTC AGC GAC GTC GAC AAC GCC GGC AAC         336
Lys Gly Ser Ala Thr Gly Phe Val Ser Asp Val Asp Asn Ala Gly Asn
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | 100 |     |     |     |     | 105 |     |     |     |     | 110 |      |
| CGT | TTC | AAT | CCG | AAC | AAG | CTG | CTG | CTC | GAC | CCC | TAC | GCG | CGC | GAG | ATC | 384  |
| Arg | Phe | Asn | Pro | Asn | Lys | Leu | Leu | Leu | Asp | Pro | Tyr | Ala | Arg | Glu | Ile |      |
|     |     |     | 115 |     |     |     |     | 120 |     |     |     |     | 125 |     |     |      |
| AGC | CAG | GAC | CCG | AAC | ACC | GCG | ACC | TGC | GCC | GAC | GGC | ACC | ATC | TAC | GCC | 432  |
| Ser | Gln | Asp | Pro | Asn | Thr | Ala | Thr | Cys | Ala | Asp | Gly | Thr | Ile | Tyr | Ala |      |
|     | 130 |     |     |     |     | 135 |     |     |     |     | 140 |     |     |     |     |      |
| ACC | GGC | GCC | GCG | CAC | CGC | AAC | AAG | GAC | AGC | GGC | CTG | TGC | GCG | AGC | AAG | 480  |
| Thr | Gly | Ala | Ala | His | Arg | Asn | Lys | Asp | Ser | Gly | Leu | Cys | Ala | Ser | Lys |      |
| 145 |     |     |     |     | 150 |     |     |     |     | 155 |     |     |     |     | 160 |      |
| GGC | ATC | GCG | CTG | GCC | GCG | GAC | GCG | ACC | TCG | GTC | GGC | AGC | AAG | CCG | ACC | 528  |
| Gly | Ile | Ala | Leu | Ala | Ala | Asp | Ala | Thr | Ser | Val | Gly | Ser | Lys | Pro | Thr |      |
|     |     |     |     | 165 |     |     |     |     | 170 |     |     |     |     | 175 |     |      |
| CGC | GCG | CTC | AAG | GAC | GAG | GTG | ATC | TAC | GAA | GTG | CAC | GTG | CGC | GGC | CTG | 576  |
| Arg | Ala | Leu | Lys | Asp | Glu | Val | Ile | Tyr | Glu | Val | His | Val | Arg | Gly | Leu |      |
|     |     |     | 180 |     |     |     |     | 185 |     |     |     |     | 190 |     |     |      |
| ACC | CGC | AAC | GAC | GAC | AGC | GTG | CCC | GCG | GCC | GAA | CGC | GGC | ACC | TAC | AAG | 624  |
| Thr | Arg | Asn | Asp | Asp | Ser | Val | Pro | Ala | Ala | Glu | Arg | Gly | Thr | Tyr | Lys |      |
|     |     | 195 |     |     |     |     | 200 |     |     |     |     | 205 |     |     |     |      |
| GGC | GCC | GCG | CGC | AAG | GCC | GCC | GCG | TTG | GCC | GCG | CTC | GGC | GTC | ACC | GCG | 672  |
| Gly | Ala | Ala | Arg | Lys | Ala | Ala | Ala | Leu | Ala | Ala | Leu | Gly | Val | Thr | Ala |      |
| 210 |     |     |     |     | 215 |     |     |     |     | 220 |     |     |     |     |     |      |
| GTC | GAG | TTC | CTG | CCG | GTG | CAG | GAA | ACC | CAG | AAC | GAC | CAG | AAC | GAT | GTC | 720  |
| Val | Glu | Phe | Leu | Pro | Val | Gln | Glu | Thr | Gln | Asn | Asp | Gln | Asn | Asp | Val |      |
| 225 |     |     |     |     | 230 |     |     |     |     | 235 |     |     |     |     | 240 |      |
| GAT | CCC | AAT | TCC | ACC | GCG | GGC | GAC | AAC | TAC | TGG | GGC | TAC | ATG | ACC | CTC | 768  |
| Asp | Pro | Asn | Ser | Thr | Ala | Gly | Asp | Asn | Tyr | Trp | Gly | Tyr | Met | Thr | Leu |      |
|     |     |     |     | 245 |     |     |     |     | 250 |     |     |     |     | 255 |     |      |
| AAC | TAC | TTC | GCC | CCG | GAC | CGC | CGC | TAC | GCC | TAC | GAC | AAG | TCG | GCC | GGC | 816  |
| Asn | Tyr | Phe | Ala | Pro | Asp | Arg | Arg | Tyr | Ala | Tyr | Asp | Lys | Ser | Ala | Gly |      |
|     |     | 260 |     |     |     |     | 265 |     |     |     |     | 270 |     |     |     |      |
| GGG | CCG | ACC | CGC | GAA | TGG | AAG | GCG | ATG | GTC | AAG | GCC | TTC | CAC | GAC | GCC | 864  |
| Gly | Pro | Thr | Arg | Glu | Trp | Lys | Ala | Met | Val | Lys | Ala | Phe | His | Asp | Ala |      |
|     |     | 275 |     |     |     |     | 280 |     |     |     |     | 285 |     |     |     |      |
| GGC | ATC | AAG | GTC | TAC | ATC | GAC | GTG | GTC | TAC | AAC | CAC | ACC | GGC | GAA | GGC | 912  |
| Gly | Ile | Lys | Val | Tyr | Ile | Asp | Val | Val | Tyr | Asn | His | Thr | Gly | Glu | Gly |      |
|     | 290 |     |     |     |     | 295 |     |     |     |     | 300 |     |     |     |     |      |
| GGC | CCG | TGG | AGC | GGC | ACC | GAC | GGG | CTC | AGC | GTC | TAC | AAC | CTG | CTC | TCG | 960  |
| Gly | Pro | Trp | Ser | Gly | Thr | Asp | Gly | Leu | Ser | Val | Tyr | Asn | Leu | Leu | Ser |      |
| 305 |     |     |     |     | 310 |     |     |     |     | 315 |     |     |     |     | 320 |      |
| TTC | CGC | GGC | CTC | GAC | AAC | CCG | GCC | TAC | TAC | TCG | CTG | AGC | AGC | GAT | TAC | 1008 |
| Phe | Arg | Gly | Leu | Asp | Asn | Pro | Ala | Tyr | Tyr | Ser | Leu | Ser | Ser | Asp | Tyr |      |
|     |     |     |     | 325 |     |     |     |     | 330 |     |     |     |     | 335 |     |      |
| AAG | TAT | CCG | TGG | GAC | AAC | ACC | GGC | GTC | GGC | GGC | AAC | TAC | AAC | ACC | CGC | 1056 |
| Lys | Tyr | Pro | Trp | Asp | Asn | Thr | Gly | Val | Gly | Gly | Asn | Tyr | Asn | Thr | Arg |      |
|     |     |     | 340 |     |     |     |     | 345 |     |     |     |     | 350 |     |     |      |
| CAT | CCC | ATC | GCC | CAG | AAC | CTG | ATC | GTC | GAC | TCG | CTG | GCG | TAC | TGG | CGC | 1104 |
| His | Pro | Ile | Ala | Gln | Asn | Leu | Ile | Val | Asp | Ser | Leu | Ala | Tyr | Trp | Arg |      |
|     |     | 355 |     |     |     |     | 360 |     |     |     |     | 365 |     |     |     |      |
| GAC | GCG | CTC | GGC | GTA | GAC | GGT | TTC | CGC | TTC | GAT | CTG | GCC | TCG | GTG | CTC | 1152 |
| Asp | Ala | Leu | Gly | Val | Asp | Gly | Phe | Arg | Phe | Asp | Leu | Ala | Ser | Val | Leu |      |
|     | 370 |     |     |     |     | 375 |     |     |     |     | 380 |     |     |     |     |      |
| GGC | AAC | AGC | TGC | CAG | CAC | GGC | TGC | TTC | AAC | TTC | GAC | AAG | AAC | GAC | TCG | 1200 |
| Gly | Asn | Ser | Cys | Gln | His | Gly | Cys | Phe | Asn | Phe | Asp | Lys | Asn | Asp | Ser |      |
| 385 |     |     |     |     | 390 |     |     |     |     | 395 |     |     |     |     | 400 |      |
| GGC | AAC | GCG | CTC | AAC | CGC | ATC | GTC | GCC | GAG | CTG | CCG | CCG | CGC | CCG | GCC | 1248 |
| Gly | Asn | Ala | Leu | Asn | Arg | Ile | Val | Ala | Glu | Leu | Pro | Pro | Arg | Pro | Ala |      |
|     |     |     |     | 405 |     |     |     |     | 410 |     |     |     |     | 415 |     |      |
| GCG | GGC | GGC | GCC | GGC | GCG | GAC | CTG | ATC | GCC | GAA | CCC | TGG | GCG | ATC | GGC | 1296 |
| Ala | Gly | Gly | Ala | Gly | Ala | Asp | Leu | Ile | Ala | Glu | Pro | Trp | Ala | Ile | Gly |      |

|         |         |         |         |         |         |         |         |         |         |         |         |         |         |         |         |      |
|---------|---------|---------|---------|---------|---------|---------|---------|---------|---------|---------|---------|---------|---------|---------|---------|------|
|         |         |         |         | 420     |         |         |         |         | 425     |         |         |         |         | 430     |         |      |
| GGC     | AAC     | TCC     | TAC     | CAG     | GTC     | GGC     | GGC     | TTC     | CCG     | GCC     | GGC     | TGG     | GCC     | GAG     | TGG     | 1344 |
| Gly     | Asn     | Ser     | Tyr     | Gln     | Val     | Gly     | Gly     | Phe     | Pro     | Ala     | Gly     | Trp     | Ala     | Glu     | Trp     |      |
|         |         | 435     |         |         |         |         | 440     |         |         |         |         | 445     |         |         |         |      |
| AAC     | GGC     | CTC     | TAC     | CGC     | GAC     | GCG     | CTG     | CGC     | AAG     | AAG     | CAG     | AAC     | AAG     | CTC     | GGC     | 1392 |
| Asn     | Gly     | Leu     | Tyr     | Arg     | Asp     | Ala     | Leu     | Arg     | Lys     | Lys     | Gln     | Asn     | Lys     | Leu     | Gly     |      |
|         | 450     |         |         |         |         | 455     |         |         |         |         | 460     |         |         |         |         |      |
| GTG     | GAA     | ACG     | GTC     | ACC     | CCC     | GGC     | ACC     | CTG     | GCC     | ACG     | CGC     | TTC     | GCC     | GGC     | TCC     | 1440 |
| Val     | Glu     | Thr     | Val     | Thr     | Pro     | Gly     | Thr     | Leu     | Ala     | Thr     | Arg     | Phe     | Ala     | Gly     | Ser     |      |
| 465     |         |         |         |         | 470     |         |         |         |         | 475     |         |         |         |         | 480     |      |
| AAC     | GAC     | CTG     | TAC     | GGC     | GAC     | GAC     | GGC     | CGC     | AAG     | CCG     | TGG     | CAT     | TCG     | ATC     | AAC     | 1488 |
| Asn     | Asp     | Leu     | Tyr     | Gly     | Asp     | Asp     | Gly     | Arg     | Lys     | Pro     | Trp     | His     | Ser     | Ile     | Asn     |      |
|         |         |         |         | 485     |         |         |         |         | 490     |         |         |         |         | 495     |         |      |
| TTC     | GTG     | GTC     | GCC     | CAC     | GAC     | GGC     | TTC     | ACC     | CTC     | AAC     | GAC     | CTG     | TAC     | GCC     | TAC     | 1536 |
| Phe     | Val     | Val     | Ala     | His     | Asp     | Gly     | Phe     | Thr     | Leu     | Asn     | Asp     | Leu     | Tyr     | Ala     | Tyr     |      |
|         |         |         |         | 500     |         |         |         |         | 505     |         |         |         |         | 510     |         |      |
| AAC     | GAC     | AAG     | CAG     | AAC     | AAC     | CAG     | CCG     | TGG     | CCG     | TAC     | GGG     | CCG     | TCC     | GAC     | GGC     | 1584 |
| Asn     | Asp     | Lys     | Gln     | Asn     | Asn     | Gln     | Pro     | Trp     | Pro     | Tyr     | Gly     | Pro     | Ser     | Asp     | Gly     |      |
|         |         | 515     |         |         |         |         | 520     |         |         |         |         | 525     |         |         |         |      |
| GGC     | GAG     | GAC     | CAC     | AAC     | CTG     | AGC     | TGG     | AAC     | CAG     | GGC     | GGC     | ATC     | GTC     | GCC     | GAG     | 1632 |
| Gly     | Glu     | Asp     | His     | Asn     | Leu     | Ser     | Trp     | Asn     | Gln     | Gly     | Gly     | Ile     | Val     | Ala     | Glu     |      |
|         | 530     |         |         |         |         | 535     |         |         |         |         | 540     |         |         |         |         |      |
| CAG     | CGC     | AAG     | GCC     | GCG     | CGC     | ACC     | GGA     | CTG     | GCG     | TTG     | CTG     | ATG     | CTC     | AGC     | GCC     | 1680 |
| Gln     | Arg     | Lys     | Ala     | Ala     | Arg     | Thr     | Gly     | Leu     | Ala     | Leu     | Leu     | Met     | Leu     | Ser     | Ala     |      |
| 545     |         |         |         |         | 550     |         |         |         |         | 555     |         |         |         |         | 560     |      |
| GGC     | GTG     | CCG     | ATG     | ATC     | ACC     | GGC     | GGC     | GAC     | GAG     | GCG     | CTG     | CGC     | ACC     | CAG     | TTC     | 1728 |
| Gly     | Val     | Pro     | Met     | Ile     | Thr     | Gly     | Gly     | Asp     | Glu     | Ala     | Leu     | Arg     | Thr     | Gln     | Phe     |      |
|         |         |         |         | 565     |         |         |         |         | 570     |         |         |         |         | 575     |         |      |
| GGC     | AAC     | AAC     | AAC     | ACC     | TAC     | AAC     | CTG     | GAT     | TCG     | GCG     | GCC     | AAC     | TGG     | CTG     | TAC     | 1776 |
| Gly     | Asn     | Asn     | Asn     | Thr     | Tyr     | Asn     | Leu     | Asp     | Ser     | Ala     | Ala     | Asn     | Trp     | Leu     | Tyr     |      |
|         |         |         | 580     |         |         |         |         | 585     |         |         |         |         | 590     |         |         |      |
| TGG     | AGC     | CGC     | AGC     | GCG     | CTC     | GAG     | GCC     | GAC     | CAC     | GAG     | ACC     | TAC     | ACC     | AAG     | CGC     | 1824 |
| Trp     | Ser     | Arg     | Ser     | Ala     | Leu     | Glu     | Ala     | Asp     | His     | Glu     | Thr     | Tyr     | Thr     | Lys     | Arg     |      |
|         |         | 595     |         |         |         |         | 600     |         |         |         |         | 605     |         |         |         |      |
| CTG     | ATC     | GCG     | TTC     | CGC     | AAG     | GCG     | CAC     | CCG     | GCG     | CTG     | CGC     | CCG     | GCG     | AAC     | TTC     | 1872 |
| Leu     | Ile     | Ala     | Phe     | Arg     | Lys     | Ala     | His     | Pro     | Ala     | Leu     | Arg     | Pro     | Ala     | Asn     | Phe     |      |
|         | 610     |         |         |         |         | 615     |         |         |         |         | 620     |         |         |         |         |      |
| TAT     | TCG     | GCC     | AGC     | GAC     | ACC     | AAC     | GGC     | AAC     | GTG     | ATG     | GAG     | CAG     | TTG     | CGC     | TGG     | 1920 |
| Tyr     | Ser     | Ala     | Ser     | Asp     | Thr     | Asn     | Gly     | Asn     | Val     | Met     | Glu     | Gln     | Leu     | Arg     | Trp     |      |
| 625     |         |         |         |         | 630     |         |         |         |         | 635     |         |         |         |         | 640     |      |
| TTC     | AAG     | CCC     | GAC     | GGC     | GCG     | CAG     | GCC     | GAC     | AGC     | GCC     | TAC     | TTC     | AAC     | GGC     | GCC     | 1968 |
| Phe     | Lys     | Pro     | Asp     | Gly     | Ala     | Gln     | Ala     | Asp     | Ser     | Ala     | Tyr     | Phe     | Asn     | Gly     | Ala     |      |
|         |         |         |         | 645     |         |         |         |         | 650     |         |         |         |         | 655     |         |      |
| GAC     | AAC     | CAC     | GCC     | CTG     | GCC     | TGG     | CGC     | ATC     | GAC     | GGC     | AGC     | GAG     | TTC     | GGC     | GAC     | 2016 |
| Asp     | Asn     | His     | Ala     | Leu     | Ala     | Trp     | Arg     | Ile     | Asp     | Gly     | Ser     | Glu     | Phe     | Gly     | Asp     |      |
|         |         | 660     |         |         |         |         | 665     |         |         |         |         | 670     |         |         |         |      |
| AGC     | GCC     | AGC     | GCG     | ATC     | TAC     | GTC     | GCC     | TAC     | AAC     | GGC     | TGG     | TCC     | GGC     | GCG     | GTC     | 2064 |
| Ser     | Ala     | Ser     | Ala     | Ile     | Tyr     | Val     | Ala     | Tyr     | Asn     | Gly     | Trp     | Ser     | Gly     | Ala     | Val     |      |
|         |         | 675     |         |         |         |         | 680     |         |         |         |         | 685     |         |         |         |      |
| GAC     | TTC     | AAG     | CTG     | CCG     | TGG     | CCG     | GGC     | ACC     | GGC     | AAG     | CAG     | TGG     | TAC     | CGG     | GTC     | 2112 |
| Asp     | Phe     | Lys     | Leu     | Pro     | Trp     | Pro     | Gly     | Thr     | Gly     | Lys     | Gln     | Trp     | Tyr     | Arg     | Val     |      |
|         | 690     |         |         |         |         | 695     |         |         |         |         | 700     |         |         |         |         |      |
| ACC     | GAT     | ACC     | GCG     | ACC     | TGG     | AAC     | GAA     | GGC     | CCC     | AAC     | GCG     | GTG     | GCG     | CTG     | CCC     | 2160 |
| Thr     | Asp     | Thr     | Ala     | Thr     | Trp     | Asn     | Glu     | Gly     | Pro     | Asn     | Ala     | Val     | Ala     | Leu     | Pro     |      |
| 705     |         |         |         |         | 710     |         |         |         |         | 715     |         |         |         |         | 720     |      |
| GGC     | AGC     | GAG     | ACC     | CTG     | ATC     | GGC     | GGC     | GAG     | AAC     | ACC     | GTC     | TAC     | GGC     | ATG     | CAG     | 2208 |
| Gly     | Ser     | Glu     | Thr     | Leu     | Ile     | Gly     | Gly     | Glu     | Asn     | Thr     | Val     | Tyr     | Gly     | Met     | Gln     |      |
|         |         |         |         | 725     |         |         |         |         | 730     |         |         |         |         | 735     |         |      |
| GCG     | CGC     | TCG     | CTG     | CTG     | TTG     | CTG     | ATC     | GCG     | AAG     | TGATAA  |         |         |         |         |         | 2244 |
| Ala     | Arg     | Ser     | Leu     | Leu     | Leu     | Leu     | Ile     | Ala     | Lys     |         |         |         |         |         |         |      |

( 2 ) INFORMATION FOR SEQ ID NO:11:

( i ) SEQUENCE CHARACTERISTICS:
        ( A ) LENGTH: 746 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Ala Ile Asp Ala Gln Gln Leu Gly Ala Arg Tyr Asp Ala Ala Gln
  1               5                  10                  15
Ala Asn Leu Ala Phe Arg Val Tyr Ser Ser Arg Ala Thr Arg Val Glu
             20                  25                  30
Val Phe Leu Tyr Lys Asn Pro Thr Gly Ser Gln Glu Val Ala Arg Leu
         35                  40                  45
Ala Leu Ser Lys Asp Pro Ala Thr Gln Val Trp Ser Leu Ser Leu Pro
     50                  55                  60
Thr Ser Thr Ile Lys Asn Thr Tyr Gly Ile Thr Gly Ala Val Tyr Tyr
 65                  70                  75                  80
Gly Tyr Arg Ala Trp Gly Pro Asn Trp Pro Tyr Asp Ala Ala Trp Thr
                 85                  90                  95
Lys Gly Ser Ala Thr Gly Phe Val Ser Asp Val Asp Asn Ala Gly Asn
                100                 105                 110
Arg Phe Asn Pro Asn Lys Leu Leu Asp Pro Tyr Ala Arg Glu Ile
            115                 120                 125
Ser Gln Asp Pro Asn Thr Ala Thr Cys Ala Asp Gly Thr Ile Tyr Ala
    130                 135                 140
Thr Gly Ala Ala His Arg Asn Lys Asp Ser Gly Leu Cys Ala Ser Lys
145                 150                 155                 160
Gly Ile Ala Leu Ala Ala Asp Ala Thr Ser Val Gly Ser Lys Pro Thr
                165                 170                 175
Arg Ala Leu Lys Asp Glu Val Ile Tyr Glu Val His Val Arg Gly Leu
                180                 185                 190
Thr Arg Asn Asp Asp Ser Val Pro Ala Ala Glu Arg Gly Thr Tyr Lys
                195                 200                 205
Gly Ala Ala Arg Lys Ala Ala Ala Leu Ala Ala Leu Gly Val Thr Ala
    210                 215                 220
Val Glu Phe Leu Pro Val Gln Glu Thr Gln Asn Asp Gln Asn Asp Val
225                 230                 235                 240
Asp Pro Asn Ser Thr Ala Gly Asp Asn Tyr Trp Gly Tyr Met Thr Leu
                245                 250                 255
Asn Tyr Phe Ala Pro Asp Arg Arg Tyr Ala Tyr Asp Lys Ser Ala Gly
                260                 265                 270
Gly Pro Thr Arg Glu Trp Lys Ala Met Val Lys Ala Phe His Asp Ala
            275                 280                 285
Gly Ile Lys Val Tyr Ile Asp Val Val Tyr Asn His Thr Gly Glu Gly
        290                 295                 300
Gly Pro Trp Ser Gly Thr Asp Gly Leu Ser Val Tyr Asn Leu Leu Ser
305                 310                 315                 320
Phe Arg Gly Leu Asp Asn Pro Ala Tyr Tyr Ser Leu Ser Ser Asp Tyr
                325                 330                 335
Lys Tyr Pro Trp Asp Asn Thr Gly Val Gly Gly Asn Tyr Asn Thr Arg
            340                 345                 350
```

-continued

| | | | | | | | | | | | | | | |
|---|---|---|---|---|---|---|---|---|---|---|---|---|---|---|
| His | Pro | Ile 355 | Ala | Gln | Asn | Leu | Ile 360 | Val | Asp | Ser | Leu | Ala 365 | Tyr | Trp | Arg |
| Asp | Ala 370 | Leu | Gly | Val | Asp | Gly 375 | Phe | Arg | Phe | Asp | Leu 380 | Ala | Ser | Val | Leu |
| Gly 385 | Asn | Ser | Cys | Gln | His 390 | Gly | Cys | Phe | Asn | Phe 395 | Asp | Lys | Asn | Asp | Ser 400 |
| Gly | Asn | Ala | Leu | Asn 405 | Arg | Ile | Val | Ala | Glu 410 | Leu | Pro | Pro | Arg | Pro 415 | Ala |
| Ala | Gly | Gly | Ala 420 | Gly | Ala | Asp | Leu | Ile 425 | Ala | Glu | Pro | Trp | Ala 430 | Ile | Gly |
| Gly | Asn | Ser 435 | Tyr | Gln | Val | Gly | Gly 440 | Phe | Pro | Ala | Gly | Trp 445 | Ala | Glu | Trp |
| Asn | Gly 450 | Leu | Tyr | Arg | Asp | Ala 455 | Leu | Arg | Lys | Lys | Gln 460 | Asn | Lys | Leu | Gly |
| Val 465 | Glu | Thr | Val | Thr | Pro 470 | Gly | Thr | Leu | Ala | Thr 475 | Arg | Phe | Ala | Gly | Ser 480 |
| Asn | Asp | Leu | Tyr | Gly 485 | Asp | Asp | Gly | Arg | Lys 490 | Pro | Trp | His | Ser | Ile 495 | Asn |
| Phe | Val | Val | Ala 500 | His | Asp | Gly | Phe | Thr 505 | Leu | Asn | Asp | Leu | Tyr 510 | Ala | Tyr |
| Asn | Asp | Lys 515 | Gln | Asn | Asn | Gln | Pro 520 | Trp | Pro | Tyr | Gly | Pro 525 | Ser | Asp | Gly |
| Gly | Glu 530 | Asp | His | Asn | Leu | Ser 535 | Trp | Asn | Gln | Gly | Gly 540 | Ile | Val | Ala | Glu |
| Gln 545 | Arg | Lys | Ala | Ala | Arg 550 | Thr | Gly | Leu | Ala | Leu 555 | Leu | Met | Leu | Ser | Ala 560 |
| Gly | Val | Pro | Met | Ile 565 | Thr | Gly | Gly | Asp | Glu 570 | Ala | Leu | Arg | Thr | Gln 575 | Phe |
| Gly | Asn | Asn | Asn 580 | Thr | Tyr | Asn | Leu | Asp 585 | Ser | Ala | Ala | Asn 590 | Trp | Leu | Tyr |
| Trp | Ser | Arg 595 | Ser | Ala | Leu | Glu | Ala 600 | Asp | His | Glu | Thr | Tyr 605 | Thr | Lys | Arg |
| Leu | Ile 610 | Ala | Phe | Arg | Lys | Ala 615 | His | Pro | Ala | Leu | Arg 620 | Pro | Ala | Asn | Phe |
| Tyr 625 | Ser | Ala | Ser | Asp | Thr 630 | Asn | Gly | Asn | Val | Met 635 | Glu | Gln | Leu | Arg | Trp 640 |
| Phe | Lys | Pro | Asp | Gly 645 | Ala | Gln | Ala | Asp | Ser 650 | Ala | Tyr | Phe | Asn | Gly 655 | Ala |
| Asp | Asn | His | Ala 660 | Leu | Ala | Trp | Arg | Ile 665 | Asp | Gly | Ser | Glu | Phe 670 | Gly | Asp |
| Ser | Ala | Ser 675 | Ala | Ile | Tyr | Val | Ala 680 | Tyr | Asn | Gly | Trp | Ser 685 | Gly | Ala | Val |
| Asp | Phe 690 | Lys | Leu | Pro | Trp | Pro 695 | Gly | Thr | Gly | Lys | Gln 700 | Trp | Tyr | Arg | Val |
| Thr 705 | Asp | Thr | Ala | Thr | Trp 710 | Asn | Glu | Gly | Pro | Asn 715 | Ala | Val | Ala | Leu | Pro 720 |
| Gly | Ser | Glu | Thr | Leu 725 | Ile | Gly | Gly | Glu | Asn 730 | Thr | Val | Tyr | Gly | Met 735 | Gln |
| Ala | Arg | Ser | Leu 740 | Leu | Leu | Leu | Ile | Ala 745 | Lys | | | | | | |

ISOAMYLASE GENE, COMPOSITIONS CONTAINING IT, AND METHODS OF USING ISOAMYLASES

RELATED APPLICATIONS

This application is a continuation-in-part of Ser. No. 08/281,902, filed Jul. 28, 1994, now abandoned.

BACKGROUND OF THE INVENTION

The majority of plant starches are composed of two polysaccharide fractions, amylopectin and amylose. Depending on the plant source, starch amylopectin content typically ranges from 70–85%, while amylose is at a corresponding 15–30%. Amylopectin, which is highly branched and bush shaped, consists of linear chains of α-1,4-linked D-glucose residues, frequently branched together, on average every 20–25 D-glucose residues, by α-1,6-D-glucosidic linkages. The amylose fraction is composed of linear α-1,4-linked D-glucose polymers and averages one α-1,6-D-glucosidic bond for every 1000 linear D-glucose residues. This essentially linear nature of amylose allows it to form a helical structure which complexes with fatty acids, low molecular weight alcohols, and iodine. While amylopectin has a molecular weight of approximately $10^7$, with a degree of polymerization of several thousand or more, amylose has a molecular weight of approximately $10^5$ with a degree of polymerization which ranges from about 900 for corn starch to 4000 for potato starch. In addition, starch from some plant varieties contains a lightly-branched, third fraction referred to as intermediate material. Although not extensively characterized, this intermediate fraction resembles both amylopectin and amylose, in that it has a has a degree of polymerization less than 1000, and may consist of only four or five branches with a chain length of 50 or more glucose residues Mutants are known in many plant species in which the ratio of amylose to amylopectin is increased. The starch products of such mutants are commercially valuable, but production is limited due to many problems, including low yields of total starch in the major crops in which such mutants are found, i.e., corn and rice. There are three maize endosperm mutants, amylose extender (ae), dull (du-1), and sugary (su-1), which contain increased amounts of amylose in their granules, but have significantly lower starch yields (Preiss, J. in *The Biochemistry of Plants*, v. 14. New York: Academic Press, 1988). A variety of potato (ND860-2) having increased amylose content is also known to have improved cold storage properties.

High amylose starches have unique properties for film formation and gelling, mainly by imparting a dramatic increase in gel strength due to amylose retrogradation. Advantages can include a) reduced oil pick-up in fried batter coatings, b) more rapid gelation (reduced drying time), and enhanced structure and texture in candies and soft jelly gums, and c) prevention of sogginess and increased crispiness in microwave foods. Furthermore, increasing the amylose content in foods such as potato and corn can bring about significant reductions in the caloric values of fried potato or corn products, mainly through a decrease in oil absorption. Finally, increasing the content of amylose has positive implications for non-food uses of starch, such as for the sizing of paper and board, for wet-end additives to pulp, and for paper lamination of corrugated boards, in the paper, packaging, and textile industries.

Isoamylase (glycogen 6-glucanohydrolase, EC 3.2.1.68) hydrolyzes the α-1,6-D-glucosidic linkages of starch, glycogen, and derived oligosaccharides, and is considered a direct debranching enzyme in that it attacks unmodified glycogen and starch, as opposed to indirect debranching enzymes which require initial polymer modification by a previous enzyme(s). Isoamylase is differentiated from the other major starch debranching enzyme, pullulanase, by its ability to cleave all the α-1,6 linkages of glycogen but not those of pullulan, whereas pullulanase completely hydrolyzes pullulan to maltotriose but has limited debranching activity on glycogen. Bacteria known to produce isoamylase include Pseudomonas sp. SMP1, *Pseudomonas amyloderomosa* SB-15, Flavobacterium sp., Cytophaga sp. (Lysobacter sp.), *Bacillus amyloliquefaciens*, and an alkalophilic strain of Bacillus.

While higher plants have been considered to have only debranching enzymes of the pullulanase type, a putative isoamylase from potato tuber has been described by Ishizaki et al., *Agric. Biol. Chem.* 47:771–779, 1983; Lee and Whelan, "Glycogen and starch debranching enzymes," p. 191–234 In P. D. Boyer (ed.), *The Enzymes*, vol 5, 1971.) Two different pullulanases were also described from the same tuber extract. The potato isoamylase had substrate specificities similar to the Pseudomonas isoamylase, but had a higher pH optimum (5.5–6.0), and consisted of a dimer with a tentative molecular weight of 178,000 Kd. The physiological role of the potato isoamylase is not well understood although it is speculated that it is involved in the enzymatic breakdown of starch during sprouting. One potato debranching enzyme activity has been reported to be pullulanase-like (by Kossman, J., et al. at the 1st Intl. Conf. on Plant Polysaccharide Engineering, Trondheim, Norway, June 1994).

It is an object of the present invention to provide a method of producing higher amylose starches. It is another object of the present invention to provide structurally modified starches having fewer α-1,6-D-glucosidic branches or an altered pattern of branching, thus having improved function properties for food and non-food uses. It is a further object of the present invention to provide DNA constructs for use in that method and plant cells containing those constructs. It is a still further object of the present invention to provide food crops having improved processing capabilities due to a structural modification of the starch content. It is a still further object of the present invention to provide transformed bacteria capable of producing an isoamylase having an improved pH optimum. It is a still further object of the present invention to provide a method of debranching starch using that isoamylase.

SUMMARY OF THE INVENTION

The present invention provides a gene for an isoamylase from Flavobacterium sp. as shown in SEQ ID NO:1. The invention further provides a DNA construct comprising in operative order:

a) a promoter which functions in plant cells to cause the production of an RNA sequence;

b) a structural coding sequence that encodes for an isoamylase; and c) a 3' non-translated region which functions in said plant cells to cause the addition of polyadenylate nucleotides to the 3' end of the RNA sequence;

wherein said promoter is heterologous with respect to the structural coding sequence and wherein said promoter is operatively linked with said structural coding sequence, which is in turn operably linked with said nontranslated region. Preferably the structural coding sequence further comprises a sequence which encodes for a plastid targeting sequence. The invention further provides plant cells transformed to contain said DNA construct. The preferred isoamylase has an optimum pH from about 5 to about 8, and the most preferred isoamylase has the sequence shown in SEQ ID NO:11.

Optionally plants transformed with the DNA construct of the present invention may contain other heterologous DNA constructs which provide other improvements. Such improvements may be unrelated to starch production, for example, herbicide resistance, disease resistance, or insect resistance. Alternatively, genes related to the production of starch in plant sink tissues may be used. Examples include granule bound starch synthases, starch branching enzymes, soluble starch synthases, and ADPglucose pyrophosphorylases. Expression of a native starch branching enzyme may also be down-regulated by using an inverted sequence (antisense) or other means in order to effect other modifications in the starch molecule. It is preferred that the plants of the present invention also contain a gene which expresses a heterologous or foreign ADPglucose pyrophosphorylase, more preferably the E. coli glgC16 gene for ADPglucose pyrophosphorylase. Its use in plants and plants transformed therewith are disclosed in WO 91/19806 (Kishore) which is equivalent to U.S. Ser. No. 08/120,703, filed Jul. 13, 1993, which is incorporated herein by reference.

The invention further provides methods of producing starch having a higher amylose content or a structurally modified starch content comprising transforming plant cells to contain said DNA construct, regenerating whole plants, multiplying said plants, harvesting materials therefrom, and extracting the starch therefrom.

The invention further provides novel plant crops having modified starch content comprising transforming plant cells to contain said DNA construct, regenerating whole plants, and harvesting the starch containing crop. Such plants crops may include the tubers of potatoes, the roots of cassava or sweet potato, and the seeds of corn, wheat, rice, or barley.

The invention further provides transformed organisms containing a gene which encodes an isoamylase having substantially the amino acid sequence shown in SEQ ID NO:11. The invention further provides the isolated isoamylase produced by such transformed bacteria which may be used in debranching starch.

As used herein, the term "isoamylase" means an enzyme capable of hydrolyzing the α-1,6-D-glucosidic linkages of starch, glycogen, and derived oligosaccharides.

As used herein, the term "modified starch content" means containing starch having amylopectin with fewer branches or an altered pattern of branching, increased intermediate material, and/or a higher ratio of amylose to amylopectin. As used herein, the term "modified starch structure" means having amylopectin with fewer branches or an altered pattern of branching, increased intermediate material, and/or a higher ratio of amylose to amylopectin. As used herein, the term "structurally modified starch" means starch having amylopectin with fewer branches or an altered pattern of branching, increased intermediate material, and/or a higher ratio of amylose to amylopectin. In all cases, the modified starch is compared to that produced by plants of the same genotype except for the introduced isoamylase gene.

DETAILED DESCRIPTION OF THE INVENTION

The present invention comprises a new method of producing plant starches having a structurally modified starch structure, preferably including a higher ratio of amylose to amylopectin, by transforming a starch producing plant with a gene for a polypeptide having the properties of an isoamylase. The gene may be derived from a variety of sources including plants and microorganisms which exhibit isoamylase activity. The preferred isoamylase has an optimum pH from about 5 to about 8, which is near the pH of the interior of an amyloplast. Such an isoamylase is provided.

For brevity of disclosure, the following detailed description of the invention will be limited to the isoamylase of Flavobacterium sp. Those skilled in the art will readily recognize that the methods described herein can be employed to utilize isoamylase genes from other sources.

Flavobacterium sp. Isoamylase

The isoamylase used in the following experiments is naturally produced by an organism, which has been characterized as a Flavobacterium species, disclosed in Sato, H. H. and Park, Y. K. Starch 32:132–136, 1980. Flavobacterium sp. was grown aerobically at 28° C. on Luria-Bertani (LB) agar, or in LB broth with shaking at 200 rpm.

For purification of isoamylase, Flavobacterium sp. was grown in 500 ml of 0.1% tryptone, 0.2% yeast extract, 0.1% casamino acids, and 0.8% maltose, with shaking at 225 rpm in 2 liter flasks at 30° C. for 20 hr. The cells were removed by centrifugation at 15,000×g, and the supernatant was filtered through a 0.2 µm filter. The cell-free supernatant was concentrated to 20 ml in an Amicon stirred cell concentrator with YM-10 membrane, and then to 2 ml in an Amicon Centriprep-30 centrifugal concentrator. The retentate was applied to an amylose/agarose affinity matrix column (2.5 cm×5 cm) pre-equilibrated with 100 mM sodium phosphate, pH 6.5 (buffer A). The column was washed with 250 ml of buffer A at 1.5 ml/min, or until no detectable protein eluted in the wash. Isoamylase was eluted from the column with 25% maltose in buffer A at 1.5 ml/min. Active one ml fractions were pooled, concentrated to 250 µl, and re-equilibrated with buffer A to remove the maltose, using Amicon Centriprep-30 and Centricon-30 centrifugal concentrators. Glycerol was added to 20% final concentration, and the isoamylase was stored at 4° C. until evaluation for purity by SDS-PAGE.

The isoamylase has a molecular weight in the range of 80–85 kD, and co-purified with a second minor band having a molecular weight in the range of 70–75 kD as determined by SDS-PAGE. It has a specific activity of approximately 50,000 units/mg protein, as determined by the standard iodine assay. [A mixture is prepared with 1 ml of 1% amylopectin, 0.2 ml of 0.2M sodium phosphate (pH 6.5), 0–0.2 ml of enzyme preparation, and water to a final volume of 1.4 ml. Upon addition of enzyme, the reaction mixture is incubated at 40° C. At various time intervals, 0.2 ml of the reaction mixture is added to 0.2 ml of 0.2% $I_2$, 2.0% KI, 0.2% $H_2SO_4$, and diluted to 10 ml with water. After 15 min at room temperature, the absorbance is read at 610 nm. One unit of isoamylase activity is defined as the amount of enzyme causing a 610 nm absorbance increase of 0.01 in one hour.]

These results differ from those reported by Sato and Park (molecular weight of 121,000 as determined by size exclusion chromatography and a final specific activity of 11,110 units/mg protein). The difference in molecular weight is probably attributable to a more accurate determination using SDS-PAGE. Furthermore, the difference in specific activity may be attributable to a protein purity difference, since purification of isoamylase to homogeneity as determined by SDS-PAGE was not presented in the original report.

N-terminal Sequencing

The purified Flavobacterium sp. enzyme (75 µg) was sequenced directly from 75 µl (3×25 µl loadings) of a 200

μM sodium phosphate, pH 6.5, solution. An Applied Biosystems, Inc. model 470A gas phase sequencer was employed for amino terminal, automated Edman degradation chemistry, using the standard sequencer cycle, 03RPTH. The respective PTH-aa derivatives were identified by RP-HPLC analysis in an on-line fashion employing an Applied Biosystems, Inc., Model 120A PTH Analyzer fitted with a Brownlee 2.1 mm I.D. PTH-C18 column. The following N-terminal sequence was determined: AIDAQQL-GARYDAAQANLAFRVYSSRATXVEXFLYKNP (SEQ ID NO:3). This sequence is 55% identical to the N-terminal sequence of the processed, mature Pseudomonas sp. isoamylase (Tognoni et al., *J. Gen. Microbiol.* 135:37–45, 1989), and indicates the probable cleavage of a signal peptide from the Flavobacterium sp. isoamylase during secretion.

Isoamylase purified to homogeneity from Flavobacterium sp. culture was also blotted onto a PVDF membrane (Immobilon, Millipore Corp.), and both major (upper) and minor (lower) bands were cut out. Samples blotted onto PVDF were sequenced directly in an N-terminal fashion using the sequencer cycle, 01RPVD. The PVDF-blotted N-terminal sequences of both bands were identical and corresponded to SEQ ID NO:3, which indicates a probable C-terminal truncation of the native enzyme in vivo or during purification.

Gene Sequencing

All basic DNA manipulations such as PCR, agarose electrophoresis, restriction digests, ligations, *E. coli* transformations, blue-white colony screens, colony lifts, and Southern blots were performed by standard protocols as described in Sambrook et al., *Molecular cloning: A laboratory manual*, 2nd ed., Cold Spring Harbor Laboratory Press, Cold Spring Harbor, N.Y, 1989.

The cell pellet from a 24 hr, 100 ml Flavobacterium sp. culture was resuspended in 3.5 ml of 10 mM EDTA, 25 mM Tris (pH 8.0), 5% glycerol, and 400 μl of 10% SDS was added. The suspension was incubated on ice for 10 min, and then frozen on dry ice for 10 min. The suspension was thawed and heated with occasional gentle rocking in a 70° C. water bath, for 5 min or until the cells lysed. The lysate was gently extracted twice with 4 ml of phenol-chloroform (1:1), then once with chloroform-isoamyl alcohol (24:1), and the DNA was precipitated by the addition of 10 ml of absolute ethanol. Without centrifugation, the supernatant was decanted, and the DNA precipitate was dissolved in 2 ml of 10 mM Tris, pH 8.0, 1.0 mM EDTA (TE8 buffer). The DNA was precipitated without centrifugation with 225 μl of 3M sodium acetate, pH 5.2, and 6.0 ml of ethanol. The precipitate was redissolved in 0.5 ml of TE8, treated with 25 μl (300 units) of DNAse-free RNAse (United States Biochemical) for 20 min at 37° C., and then extracted with an equal volume of phenol-chloroform. The DNA was precipitated, redissolved in TE8 buffer, and dialyzed against TE8 buffer (4×1.0 l) for 18 hr.

A DNA probe for isoamylase was generated by PCR amplification from Flavobacterium sp. chromosomal DNA. Degenerate PCR primers were designed from two highly conserved, consensus amino acid sequences among bacterial glucanases. These are SEQ ID NO:8 and SEQ ID NO:9. Specifically, the enzyme sequences used were for Pseudomonas sp. isoamylase, *Klebsiella pneumoniae* pullulanase, and *Bacillus stearothermophilus* neopullulanase. The oligonucleotide primers were also designed with a high GC content to reflect the high GC content of the Flavobacterium genome.

The PCR cycling conditions were as follows: 94° C., 3'; 60° C., 2'; 72° C., 3' (5 cycles); 94° C., 30s; 60° C., 2'; 72° C., 3' (30 cycles). The 260 bp PCR product was gel purified, ligated into the EcoRV site of pBSSK+, and clones were isolated by a blue-white screen as described in Sambrook et al.

The nucleotide sequence of the 260 bp PCR product, generated from Flavobacterium sp. chromosomal DNA, is SEQ ID NO:4. Sequence analysis shows it to be 56% identical at the amino acid level to the same region within the Pseudomonas sp. isoamylase as published by Tognoni et al. This 260 bp fragment was random prime-labelled with digoxigenin according to the Genius™ Nonradioactive DNA Labelling System.

Flavobacterium sp. genomic DNA was individually digested to completion with BamHI, BglII, ClaI, EcoRI, NotI, PstI, SacI, and XhoI. The digests were Southern blotted onto Zeta-Probe membranes (Bio-Rad), baked under vacuum at 80° C. for 1 hr, probed with the digoxigenin-labelled 260 bp fragment, and detected as recommended by the Genius™ Nonradioactive Detection System. Hybridization was overnight at 68° C., and final washings were with 0.2×SSC, 0.1% SDS at 68° C. A single probe-positive band was obtained for each digest, with BglII, NotI, and PstI giving a band of approximately 10 kb, 9 kb, and 5 kb, respectively. Genomic BglII fragments (9–12 kb), NotI fragments (7–10 kb), and PstI fragments (4–6 kb) were isolated by preparative agarose gel electrophoresis, and ligated into their respective, dephosphorylated sites in pBSSK+. The ligations were transformed into *E. coli* DH5α, and transformant colonies were lifted onto Hybond™-N+ nylon membranes. The membranes were laid colony-side up on fresh LB-ampicillin plates and incubated at 37° C. for 4 hours. Colonies were lysed by placing membranes for 5 min, consecutively, on Whatman 3MM paper saturated with 10% SDS, followed by 0.5M NaOH, 1.5M NaCl, followed by 1M Tris-HCl, pH 8.0, 1.5M NaCl. Cell debris was completely removed by washing with 5×SSC, and the membranes were baked under vacuum at 80° C. for 1 hr.

Hybridization of the same 260 bp probe (SEQ ID NO:4) and detection were essentially as described for Southern blots. Putative probe-positive colonies were prepared for plasmid DNA, and verified for probe-positive inserts by Southern blot hybridization. In order to screen for isoamylase activity, *E. coli* SR193 containing pGP1–4 was individually transformed with two NotI probe-positive clones, three PstI probe-positive clones, and pBSSK+ as control. *E. coli* SR193 contains a temperature sensitive, excision-defective lambda prophage. When colonies grown at 28° C. are transferred and incubated at 37° C., the lambda lytic genes are induced and colonies become "porous" due to cell wall degradation. pGP1–4 is a ColE1-based plasmid which contains the bacteriophage T7 RNA polymerase under control of the temperature inducible lambda $P_L$ promoter, and the gene for the heat-sensitive lambda repressor, cI857 (Tabor et al., Proc. Natl. Acad. Sci. USA, 82:1074–1078, 1985). Transformations were plated on LB agar containing amylopectin (1%), ampicillin, and kanamycin, and assayed for isoamylase expression using the plate detection assay. [Isoamylase plate detection assay: After an initial incubation at 28° C. for 20 hr, or until colonies were 1 mM in diameter, the plates were transferred to 37° C. for an additional 20 hr to induce cell wall leakiness (lambda lytic genes) and T7 RNA polymerase transcription. The plates were inverted over several drops of a 2% $I_2$, 1% KI, 25% ethanol solution, and isoamylase activity was detected by a blue halo surrounding the colonies (due to the formation of amylose from amylopectin).]

The NotI clones did not show isoamylase activity; however, the PstI clones exhibited an intense blue halo surrounding the colonies due to the release of active isoamylase. One active isolate with a 4.9 kb PstI insert was chosen for all subsequent analyses, and was designated pMON17481.

Restriction fragments from the PstI insert of pMON17481 were subcloned in both orientations in pBSSK+ and pBSKS+. Single-stranded DNA was prepared from *E. coli* JM101 carrying pMON17481 derivatives, after superinfection with M13K07 helper phage (Bio-Rad). Single-stranded DNA was purified using the ssPhage™ DNA Isolation Kit from Bio 101, and sequenced by the dideoxy chain termination method using the TAQuence™ Version 2.0 DNA Sequencing Kit from United States Biochemical. Custom synthesized primers were used to sequence in both directions, with and without 7-deaza-dGTP, the Flavobacterium sp. isoamylase open reading frame and the 5' and 3' untranslated regions. Sequence analysis was performed using the University of Wisconsin GCG Sequence Analysis Software Package.

The nucleotide sequence thus determined is shown in SEQ ID NO:1. Sequence analysis revealed a 2334 bp open reading frame that encodes a 777 amino acid pre-enzyme. This translation (SEQ ID NO:2) has a predicted molecular weight of 84,340.

Expression in *E. coli*

Using pMON17481 as template, PCR mutagenesis was performed to remove the microbial signal sequence from the cloned gene. The following primers were designed to add a methionine residue to the beginning of the processed mature isoamylase (alanine-33) to allow translational initiation, and an additional stop codon (TAA) 3' adjacent to the endogenous TGA codon. The primers also included N-terminal NcoI and C-terminal SacI and EcoRI sites.

N-terminal: 5'-GGGGCCATGGCCATCGATGCGCAGCA GCTCGGCGCGCGCTACGAC-3' (SEQ ID NO:5)

C-terminal: 5'-CCCCGAATTCGAGCTCTTATCACTTCG CGATCAGCAACAGCAGCGA-3' (SEQ ID NO:6).

PCR reactions required either 5%, formamide or 10% DMSO, final concentration, due to the high GC content of the coding sequence. PCR cycling conditions were as follows: 96° C., 3'; 65° C., 2'; 72° C., 3' (5 cycles); an additional 5 units of Taq polymerase were added per reaction, followed by 94° C., 30s; 65° C., 2'; 72° C., 3'+20 sec/cycle (30 cycles). The 2.3 kb PCR product (SEQ ID NO:10) was gel purified and cloned into the NcoI-EcoRI sites of a pUC-based *E. coli* cloning vector in which a modified polylinker is located within the lacZ α-peptide gene and expression is driven by the lac promoter. Clones with the 2.3 kb insert (SEQ ID NO:10) were identified in *E. coli* JM101 using a blue-white screen. The protein expressed has the sequence shown in SEQ ID NO:11.

Isoamylase was also prepared from liquid cultures of *E. coli* JM101 transformants [25 ml of LB-ampicillin broth, 200 rpm, at 37° C., and inducing expression with 0.5 mM IPTG, at optical density (610 nm) of 0.5]. Cells were pelleted at 3 hr post-induction, resuspended in 500 µl of 100 mM sodium phosphate, pH 6.5, and sonicated (Heat Systems-Ultrasonics, Inc., Model W-375) on ice for 2×10 sec bursts at 30% relative maximum output. The crude lysate was centrifuged at 12,000×g for 5 min, and debranching activity was measured in the supernatant by the standard iodine assay described above.

The isolate producing the highest level of isoamylase activity, pMON17408, was chosen and the 2.3 kb insert (SEQ ID NO:10) was subcloned into the NcoI-EcoRI sites of an *E. coli* expression vector to give pMON17409. This vector contains the pACYC replicon and the ribosome binding site of the synthetic G10 leader sequence in which expression is driven by the tac promoter. High level isoamylase expression from pMON17409 in *E. coli* JM101 was achieved by induction with IPTG of a 500 ml LB-kanamycin culture, as described above. At times 0, 1, 2, and 3 hr, post-induction, 1 ml aliquots were removed from the culture, pelleted, resuspended in a volume (µls) of Laemmli sample buffer that corresponded numerically to the optical density in Klett units, and boiled for 8 min. The appearance of a new, highly-expressed 80–85 Kd protein was determined by SDS-PAGE. The remaining cells were pelleted at 3 hr post-induction, resuspended in 8 ml of 100 mM sodium phosphate, pH 6.5, sonicated on ice for 2×20 sec bursts, and centrifuged at 15,000×g for 5 min.

Isoamylase from the intracellular crude supernatant from a 500 ml culture was purified to homogeneity as described above. The purified recombinant isoamylase was verified for cross reactivity with anti-Flavobacterium sp. isoamylase polyclonal antibodies by western blot analysis. Interestingly, the minor 70–75 Kd band seen with extracellular isoamylase purified from Flavobacterium sp. was not detected, and suggests that the C-terminal truncation of the donor enzyme was due to cleavage by a Flavobacterium protease. The purified recombinant enzyme (SEQ ID NO:11) had a specific activity of approximately 50,600 Units/mg, which is similar to that determined for purified donor enzyme, and had the same molecular weight as determined by SDS-PAGE.

Other Hosts for Fermentation

The isoamylase of the present invention (SEQ ID NO:11) can be produced in and prepared from a variety of host organisms. The gene for producing this enzyme in a host organism may be the gene (SEQ ID NO:1) for the immature sequence having a signal sequence for secretion or the gene (SEQ ID NO:10) for the mature sequence. Alternatively, a secretion signal sequence native to the host organism may be used.

*E. coli* transformed as described above may be used to prepare the isoamylase by fermentation. Alternatively, a Bacillus sp. may be used as described in *Molecular Biological Methods for Bacillus*, Harwood et al. (eds.), New York: Wiley-Interscience, 1990. See also F. G. Priest, *Aspects of Microbiology*, 9, *Extracellular Enzymes*, Washington: American Society for Microbiology, 1984.

Yeast species are also useful in producing heterologous polypeptides. One of skill in the art will be familiar with the mechanism for transformation and fermentation of yeasts. General directions may be found in (1) *Biotechniques*, 13(1): 18–19, 1992; and (2) *Current Opinion in Biotechnology*, 3:486–496, 1992.

Alternatively, insect cells can be made to produce a desired peptide, e.g., Flavobacterium sp. isoamylase, by infecting cell cultures with transformed baculovirus particles. See Summers, et al. *Texas Exp. Station Bull.* 1555:1–57.

Use in Debranching Starch

The isoamylase produced by recombinant *E. coli* or other organisms can be used in the production of various products from plant starches. Debranching is one step in the production of high fructose corn syrup from corn starch. The properties of this particular debranching enzyme make it particularly suitable for those applications where a near neutral pH would be advantageous. Currently, Pseudomonas isoamylase, having pH optimum of 3–4, is the only commercial isoamylase available for starch structure analysis and starch processing for food use. Recently PCT application WO 94/13792 reported the discovery of an amylase from *Bacillus licheniformis* having a pH optimum of 4.0–5.5. Its use in "liquefying corn starch" to produce glucose without adjusting the pH was stated to be an advantage. Therefore, use of Flavobacterium sp. isoamylase could provide a still further improvement in this process because it will function at a pH even closer to neutral.

The pH optimum for purified, pMON17409-produced isoamylase was determined under standard iodine assay conditions in 50 mM acetate, 50 mM MES, 100 mM Tris buffer, over the pH range of 4–9.5. Initial linear velocities were used to calculate relative activities (% of maximum). For pH stability profile, the purified, pMON17409 isoamylase was reequilibrated to 8 mM sodium phosphate, pH 6.5, 20% glycerol, by an Amicon centricon-30 concentrator. To 3.5 µl of enzyme, 2.0 µl of a 175 mM acetate, 175 mM MES, 350 mM Tris stock buffer was added, to give a final concentration of 64 mM acetate, 64 mM MES, 127 mM Tris. The enzyme was then incubated at 40° C. for 30 min. over a pH range of 4.5–9.5. Residual isoamylase activity of the 5.5 µl mixture was then determined by the standard iodine assay, in 50 mM acetate, 50 mM MES, 100 mM Tris, pH 6.5, final concentration.

The results indicated a pH optimum of 6.0–7.0, which is similar to the previously reported value of 6.3 for the donor enzyme (Sato and Park). The optimum stability is at pH 6.5–7.0. However, when assayed at 22° C., recombinant isoamylase displayed broader activity and stability optima of pH 5.0–8.0.

Substrate specificities for purified, recombinant isoamylase from pMON17409 were determined for oyster glycogen, rabbit liver glycogen, corn amylopectin, rice starch, potato starch, and pullulan. Specific activities were determined from initial rates of hydrolysis at pH 6.5. The relative rates of debranching of various branched polysaccharides by purified recombinant isoamylase are shown in Table 1. The enzyme had highest substrate specificity for glycogen, but scarcely hydrolyzed pullulan, which corroborates that the purified enzyme is an isoamylase.

TABLE 1

| Substrate | Specific activity* |
| --- | --- |
| Oyster glycogen | 182 |
| Rabbit liver glycogen | 174 |
| Corn amylopectin | 172 |
| Rice starch | 154 |
| Potato starch | 120 |
| Pullulan | 3 |

*S.A. = µmoles reducing groups released/min/mg protein.

Transformation of Plants

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Transcription of DNA into mRNA is regulated by a region of DNA usually referred to as the promoter. The promoter region contains a sequence of bases that signals RNA polymerase to associate with the DNA, and to initiate the transcription of mRNA using one of the DNA strands as a template to make a corresponding complimentary strand.

Promoters which are useful in the present invention are those which will initiate transcription in tissues in which starch is produced. Such promoters may be derived from the plant species to be transformed or may be heterologous to such plant. Examples of promoters useful in the present invention are those which will function in potato tubers. These include the promoters for granule bound starch synthases, soluble starch synthases, ADPglucose pyrophosphorylases, patatins (Class I), sucrose synthases, branching enzymes, debranching enzymes, and tuber polyphenol oxidases (GenBank® Accession Numbers M95196 and M95197).

Promoters which will cause the production of an isoamylase in a seed are useful in the present invention. From any plant seed, one may obtain the genes for enzymes involved in the production of starch and use those promoters in the DNA constructs of described herein. Thus native promoters for corn, wheat, rice, and barley may be obtained and used in the present invention.

Examples of promoters which will function in the seeds of corn include the zein promoters. The zeins are a group of storage proteins found in maize endosperm. Genomic clones for zein genes have been isolated and published, and the promoters from these clones, including the 15 kD, 16 kD, 19 kD, 22 kD, 27 kD, and gamma genes, could also be used to express an isoamylase gene in the seeds of corn and other plants. Other promoters known to function in corn include the promoters for the following genes: waxy, brittle 2, shrunken 2, branching enzymes I and II, starch synthases, debranching enzymes, oleosins, glutelins, and sucrose synthases.

Examples of promoters suitable for expression of an isoamylase gene in wheat include those for the genes for the ADPGPP subunits, for the granule bound and soluble starch synthases, for the branching and debranching enzymes, for the embryogenesis-abundant proteins, for the gliadins, and for the glutenins. Examples of such promoters in rice include those for the genes for the ADPGPP subunits, for the granule bound and soluble starch synthases, for the branching enzymes, for the debranching enzymes, for the sucrose synthases, and for the glutelins. Examples of such promoters for barley include those for the genes for the ADPGPP subunits, for the granule bound and soluble starch synthases, for the branching enzymes, for the debranching enzymes, for the sucrose synthases, for the hordeins, for the embryo globulins, and the aleurone specific proteins.

The plants which are amenable to transformation and use in the present invention are many. Examples include, but are not limited to, corn, potato, rice, barley, sweet potato, cassava, and wheat. Each of these plants may be transformed by one of ordinary skill in the art using known methods.

Introns

In general, optimal expression in monocotyledonous plants is obtained when an intron sequence is located between promoter and coding sequences. Examples of such intron sequences are Adh1 and Hsp70 introns. The Hsp70 intron described in WO 93/19189 is preferred.

Plastid Targeting Sequence

The DNA constructs of the present invention may optionally contain a plastid targeting sequence. If they do not contain such a sequence, the enzyme translated from the structural coding sequence will be generally found in the cytoplasm of the cell. Such cytosolic enzyme would be useful in the production of food products because it would lead to debranching of starch during processing of the product from the raw plant part. For example, cutting potato tubers disrupts the starch granules contained therein, making the starch available for debranching by cytosolic isoamylase. The processed potato product would then have the improved properties noted above, such as reduced oil pickup and improved texture.

Optionally, the DNA construct may be prepared with a plastid targeting sequence. Such a targeting sequence causes the protein to be imported into the plastid; the targeting sequence is removed during importation. It is believed that chloroplast and amyloplast targeting sequences will each function to move a protein into either type of plastid. The use of both types is within the present invention.

The preferred targeting sequence is a modified chloroplast targeting sequence (CTP) derived from the sequence reported by Timko et al. in "Genetic Engineering of Nuclear Encoded Components of the Photosynthetic Apparatus in Arabidopsis" in *Impact of Chemistry on Biotechnology—A Multidisciplinary Discussion*, ed. by Phillips, et al., pp 279–295, 1988. This modified targeting sequence (CTP1) was reported by Stark et al., "Regulation of the amount of starch in plant tissues by ADP glucose pyrophosphorylase," *Science* 258:287–292, 1992, and is shown in SEQ ID NO:7.

A fusion of the selected plastid targeting sequence and an isoamylase gene may be made by standard procedures and used in the present invention.

Polyadenylation Signal

The 3' non-translated region of the chimeric plant gene contains a polyadenylation signal which functions in plants to cause the addition of polyadenylate nucleotides to the 3' end of the RNA. Examples of suitable 3' regions are (1) the 3' transcribed, non-translated regions containing the polyadenylated signal of Agrobacterium the tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gene.

Isoamylase Gene Sources

The isoamylase gene used in the DNA constructs for plant transformation of the present invention may be any isoamylase gene. It is not limited to the Flavobacterium sp. gene described above, although it is preferred. If the enzyme is not targeted to the plastid as described above, the pH optimum requirements may not be as strict. An isoamylase gene from a Pseudomonas or a Bacillus may be used, for example. Genes already in use for the commercial production of isoamylases may be moved into plasmids containing plant-appropriate regulatory sequences and used in the present invention.

Another possibility is the use of a gene for a plant isoamylase, for example, a native potato isoamylase, which is engineered behind a promoter which will cause production of the isoamylase during starch metabolism in a sufficient amount to cause production of modified starch. Thus, the potato isoamylase enzyme activity could be moved from sprouting to starch production. Assays described here can be used for complementation cloning of isoamylase genes from plant sources from expression libraries and the gene thus obtained can be substituted for a bacterial isoamylase gene. Alternatively, the isoamylase gene from plant sources can be obtained by purification of the protein, amino acid sequencing, and gene isolation using well known techniques.

In order to isolate such genes, the DNA primers shown below as SEQ ID NO:8 and SEQ ID NO:9, or related primers with more or less bias for genes with lower or higher G+C percent content, may be used with PCR techniques to clone an isoamylase gene. Alternatively, SEQ ID NO:4, which is an internal region of the Flavobacterium sp. gene described above, may be used as a probe to isolate other isoamylase genes.

The following examples use the isoamylase gene from Flavobacterium sp. (hereafter iam), but should not be interpreted in any way to limit the scope of the present invention. Those skilled in the art will recognize that various other genes as well as modifications, truncations, etc., can be made to the methods and genes described herein while not departing from the spirit and scope of the present invention. For example, mutagenesis and screening may be employed to produce mutant derivatives of the other known isoamylases discussed above which will have pH optima closer to the preferred 5–8 range.

Expression in Potato

In order to obtain tuber specific expression, a vector (pMON16953) was constructed to contain a ~1.0 kb portion of the tuber-specific class I patatin promoter (hereafter, "Ppatatin1.0, described by Bevan et al., *Nucleic Acids Res.* 14:4625:4638, 1986), the 3'-nontranslated polyadenylation region of the nopaline synthase gene (NOS 3'), and spectinomycin resistance for selection in *E. coli* and *Agrobacterium tumefaciens*. The iam gene was isolated as an NcoI-EcoRI fragment from pMON17409. The modified chloroplast transit peptide (CTP1) gene (SEQ ID NO:7) as a BglII-NcoI fragment was fused to the translation initiation site of the iam gene by a triple ligation into the BglII-EcoRI sites of pMON16953, to give PMON17411. The Ppatatin1.0/CTP1-iam/NOS3' NotI expression cassette from pMON17411 was ligated into the unique, dephosphorylated NotI site of pMON17227 and pMON17320, to give pMON17418 and pMON17419, respectively. pMON17227 is a Ti plasmid vector disclosed and described by Barry et al. in WO 92/04449 (1991), incorporated herein by reference, which contains the FMV/CP4 construct for glyphosate selection in plant transformation and regeneration. pMON17320 is a pMON17227 derivative which also contains a Ppatatin 1.0/CTP1-glgC16 cassette. The CTP1-glgC16 fusion encodes a modified ADPglucose pyrophosphorylase as described by Kishore in WO 91/19806.

Both pMON17418 and pMON17419 constructs were screened in *E. coli* MM294 for clockwise orientation to FMV/CP4. Both pMON17418 and pMON17419 were mobilized into a disarmed ABI *Agrobacterium tumefaciens* strain by the triparental conjugation system using the helper plasmid pRK2013 (Ditta et al. 1980).

To transform Russet Burbank potato using glyphosate as a selectable marker, the appropriate Agrobacterium was grown overnight in 2 ml of LB broth supplemented with 75 µg/ml of spectinomycin, 75 µg of kanamycin, and 50 µg/ml of chloramphenicol. The overnight culture was diluted 1:10 with MSO, or until an optical density 600 nm of 0.2–0.33 was established. Leaves were removed from the stems of potato plants that had been grown under sterile conditions for three weeks on PM media supplemented with 25 mg/ml ascorbic acid. The stems were cut into 3–5 mm segments and inoculated with diluted bacteria for 15 min in square petri dishes. Explants were placed onto co-culture plates which contained 1/10 MSO with 1.5 ml of TxD (tobacco feeder) cells overlain with wetted filter paper. About 50 explants were placed per plate. After 2 days co-culture period, explants were placed onto callus induction media, which contained 5.0 mg/l Zeatin Riboside, 10 mg/l AgNO$_3$, and 0.1 mg/l napthaline acetic acid, for 2 days. Explants were subsequently transferred onto callus induction media which contained 0.025 mM glyphosate for selection. After 4 weeks, explants were placed onto shoot induction media which contained 5.0 mg/l Zeatin Riboside, 10 mg/l AgNO$_3$, 0.3 mg/l gibberellic acid, and 0.025 mM glyphosate. Shoots began to appear at 8 weeks. Explants were transferred to fresh shoot induction media every 4 weeks for 12 weeks. Shoots were excised and placed on PM media for about 2 weeks or until they were large enough to be placed into soil. Growth chamber conditions the first 2 months included a 14 hr photoperiod with light intensity of 600 µE, 60% relative humidity, fertilization, and 25° C. day/19° C. night incubation. The third month conditions were modified to a 12 hr photoperiod, no fertilization, and 25° C. day/12° C. night incubation, after which tubers were harvested.

Analysis of Tubers from Transformed Potatoes

Out of 24 lines transformed with pMON17419, several showed an increase in tuber specific gravity similar to that previously reported for potatoes containing the glgC16 gene.

Mature, greenhouse-grown tubers, both control and transformed, were processed, without extraction buffer, through a Braun high speed juicer, followed by immediate centrifugation at 2000×g for 5 min to pellet the starch granules. The supernatant was frozen on dry ice and stored at −80° C. Western analysis of the supernatant of the juiced tuber extract indicated the presence of new bands that had lower molecular weights than Flavobacterium sp. isoamylase, perhaps due to proteolysis. This occurred even in the presence of protease inhibitors.

The pelleted starch granules were washed and centrifuged six times with several volumes of cold (4° C.) water, followed by two cold (−20° C.) acetone washes. The granules were air dried and stored at 4° C.

For western blot analysis, 1.0 g of these granules was vortexed for 3 min in 10 ml of 1.0% SDS, 50 mM Tris-HCl, pH 7.5, to strip granule surface proteins, and centrifuged at 2000×g for 5 min. The procedure was repeated, the granules were washed 5 times in 10 ml of water, and then washed twice with 5 ml of acetone. Proteins internally-embedded within the granule were extracted from SDS-washed granules by boiling 100 mg granules in 1.0 ml of Laemmli sample buffer for 6 min. The Laemmli-starch gel was macerated in the microfuge tube with a 200 µl pipette tip, and centrifuged at 12,000×g for 10 min. The supernatant (approximately 0.4 µg of protein loaded per lane) underwent SDS-PAGE, followed by western blot to determine the isoamylase protein level within the granule. Western analysis of these SDS-washed granules extracted with Laemmli sample buffer showed that 18 out of 23 lines transformed with pMON17419 contained Flavobacterium sp. isoamylase within the granules, at the same molecular weight as the E. coli-expressed isoamylase. Isoamylase levels, estimated by western blot, ranged between 0.5–3.0% of total granule-extracted protein. While isoamylase appeared to be proteolytically degraded during tuber extraction, western analysis of proteins extracted from SDS-washed granules showed isoamylase to be protected from proteolysis. The results demonstrated that isoamylase was not only imported within the amyloplast but was embedded inside the granule matrix. The presence of isoamylase during starch biosynthesis probably allowed the enzyme to become entrapped within the starch network as the growing starch molecules crystallized.

Starch granules stored at 4° C. were analyzed by light microscopy using a Nikon Diaphot-TMD inverted microscope. Granules (50 mg) were suspended in 2 ml of water, and 100 µl of the suspension was visualized under cover slip at 100×, 200×, and 400× magnification. pMON17419 granules containing isoamylase displayed gross morphological alterations. Several pMON17419 lines produced isoamylase-containing granules that were elongated, cylindrical, spindle-like, angular, less spheroidal, less symmetrical, and highly irregular in shape. However, the expression level of isoamylase, as determined by western blot, did not always correlate perfectly with the degree of granule irregularity. In comparison, wild type lines, or lines transformed only with glgC16, produced granules which were oval, spheroidal, and symmetrical.

Particle size distribution was determined for starch granules using a Coulter LS 130 Series Particle Size Analyzer with the Micro Volume Module. Granule suspensions (40 mg/10 ml of water) were sonicated 1 min followed by rapid mixing with a magnetic stir bar (3.5 setting) for 1 min. Preliminary analysis determined that a 1 min sonication time had no effect on particle size. Duplicate size determinations were obtained for 800 µl aliquots from the sonicated suspensions.

Table 2 summarizes the expression level estimated by western blot and the subjective degree of irregularity in granule shape for all pMON17419 lines, and the particle size analysis for selected lines. A scale of 0 to 10 was used for granule irregularity with 0 being normal and 10 being extremely deformed. The particle size analysis was not adjusted for the different shape of the transgenic granules. The data indicate smaller granules for lines 3, 19, and 25.

TABLE 2

| Lines | °Irregular (0–10 scale) | Isoamylase by Western | Vol. Diameter (µM) | |
|---|---|---|---|---|
| | | | Mean | Med. |
| Wild type-1 | 0 | Neg | 35.06 | 35.37 |
| Wild type-2 | 0 | Neg | 34.50 | 34.32 |
| Wild type-3 | 0 | Neg | 34.76 | 35.10 |
| 17419-1 | 8 | High | 35.30 | 35.45 |
| 17419-2 | 5 | Med | | |
| 17419-3 | 2 | Med | 30.88 | 30.84 |
| 17419-4 | 6 | High | 35.34 | 34.60 |
| 17419-5 | 2 | Med | | |
| 17419-6 | 10 | High | 34.74 | 33.64 |
| 17419-12 | 8 | Med | | |
| 17419-13 | 5 | Med | | |
| 17419-14 | 8 | High | | |
| 17419-15 | 7 | Med | | |
| 17419-16 | 0 | Neg | | |
| 17419-17 | 4 | — | | |
| 17419-18 | 0 | Neg | | |
| 17419-19 | 7 | High | 32.92 | 32.22 |
| 17419-20 | 3 | High | | |
| 17419-21 | 10 | High | 34.30 | 33.82 |
| 17419-22 | 0 | Neg | | |
| 17419-23 | 3 | Low | | |
| 17419-25 | 0 | High | 32.98 | 32.37 |
| 17419-26 | 8 | Med | | |
| 17419-27 | 0 | Neg | | |
| 17419-29 | 5 | Low | | |
| 17419-30 | 9 | High | | |

The effect of the modifications caused by iam on the thermogelation properties of starch was studied with differential scanning calorimetry using a Perkin-Elmer model DSC-7 instrument. Starch samples (3.0+/−0.1 mg) were weighed into Perkin-Elmer aluminum volatile sample pans and 10 µl of distilled deionized water was added. The sample pans were hermetically sealed and reweighed. Samples were immediately scanned from 20° C. to 90° C. at 10° C. per minute. Samples were reweighed afterwards to ensure there was no weight loss. Temperatures and enthalpy values were determined using Perkin Elmer System 7 software, except for the extrapolated final temperature ($T_m$) values which had to be determined manually. The results are shown in Table 3. The values are the mean±the standard deviation. For Wild type-1, n=4; Wild type-2 and type-3, n=2; Lines 6, 21, and 30, n=3.

TABLE 3

| Source | Endothermic transitions (°C.) | | | Enthalpy of gelation (Joules/gm) |
|---|---|---|---|---|
| | Onset temp. | Peak temp. | End temp. | |
| Wild type-1 | 63.9 ± 0.27 | 67.1 ± 0.21 | 70.5 ± 0.25 | 16.72 ± 0.23 |
| Wild type-2 | 66.3 ± 0.07 | 69.5 ± 0.07 | 73.4 ± 0.07 | 16.77 ± 0.28 |
| Wild type-3 | 63.5 ± 0.14 | 66.6 ± 0.14 | 71.4 ± 0.0 | 16.85 ± 0.30 |
| pMON17419 | | | | |
| Line 6 | 63.0 ± 0.35 | 66.1 ± 0.29 | 69.5 ± 0.35 | 16.93 ± 0.68 |
| Line 21 | 60.9 ± 0.25 | 65.0 ± 0.20 | 69.2 ± 0.10 | 16.17 ± 0.41 |
| Line 30 | 61.6 ± 0.21 | 65.9 ± 0.06 | 70.0 ± 0.06 | 16.26 ± 0.38 |

The gelation properties of the transgenic granules, as determined by DSC, corroborate the changes in granule morphology. The lower gelatinization temperatures for the iam-glgC16 granules suggest a higher amount of intermediate material due to an alteration of the elongation to branching ratio. Furthermore, starch granules with higher gelatinization temperatures typically have a higher degree of crystallinity, which provides structural and thermal stability to the granules. The DSC results also indicate the transgenic granules have 1) an overall less-highly ordered crystalline structure, and/or 2) fewer crystalline regions that are thermally and structurally more stable, and/or 3) less-stable amorphous regions. Therefore, a perturbation of the starch biosynthetic machinery by isoamylase activity may have created intermediate material that is less able to form a high degree of crystallinity.

High performance anion exchange chromatography (HPAEC) was performed with a Dionex system consisting of a GP40 gradient pump, an eluant organizer pressurized with helium, an ED40 pulsed amperometric detector (PAD-II), a post-column pneumatic controller, and an AS3500 autosampler (Thermo Separations Products). The PAD-II utilized a gold working electrode and a silver-silver chloride reference electrode. Data integration and analysis were performed using the Dynamax® MacIntegrator™, ChromPic™, and Dynamax® Compare Modules software package from Rainin Instrument Co.

Starch samples from lines 6, 21, and 30 (lines having the highest degrees of granule shape irregularity) were prepared for HPAEC by dissolving 75 mg of purified starch granules in 5 ml of 0.1N sodium hydroxide, adding 7.5 ml of water, and boiling 15 min. The solution was adjusted to approximately pH 4.0 with 2.5 ml of 1.0M sodium acetate, pH 3.5. One ml was removed; 200 units (10–30 µl) of Pseudomonas sp. isoamylase (desalted by Amicon centricon-30) were added; and the reaction incubated at 37° C. for 4 hr, or until no further increase in reducing groups was determined by the Somogyi-Nelson method (Hodge and Hofreiter, in *Methods in carbohydrate chemistry*, New York: Academic Press, 1962). A 500 µl aliquot of the starch solution was desalted through a Quick Spin™ G-25 sephadex column previously equilibrated with water. The eluant was adjusted to pH 12 with 3 µl of 50% sodium hydroxide, and filtered through a 0.45 µm membrane. Sample injection volume was 25 µl. Chain length distribution was determined using a CarboPac PA-1 column (Dionex, 4×250 mm) with an in line filter (5 µm, 35 µm). Eluent A was 150 mM sodium hydroxide, and eluent B was 150 mM sodium hydroxide containing 500 mM sodium acetate. The sodium acetate elution gradient was as follows: 30% of eluent B at 0 min; 40% at 2.0 min; 60% at 20 min; 80% at 50.0 min; 80% at 55.0 min. The PAD-II pulse potentials (volts) and durations (s) were as follows: $E_1$ 0.05 ($t_1$ 0), $E_2$ 0.05 ($t_2$ 0.2), $E3$ 0.05 ($t_3$ 0.5), $E_4$ 0.6 ($t_4$ 0.51), $E_5$ 0.6 ($t_5$ 0.59), $E_6$ −0.6 ($t_6$ 0.6), $E_7$ −0.6 ($t_7$ 0.65). High purity malto-oligosaccharides (G2–G7) (Hayashibara Co.) were used to construct a standard response curve.

Chain length distribution, as determined by HPAEC, indicated distinct differences between starch extracted from wild type lines and transgenic lines. Chromatograms of starch from pMON17419 lines 6, 21, and 30 showed a significantly higher percentage of long branch chains having a degree of polymerization of 30 and higher, in comparison to wild type lines. The results indicate that the transgenic starch contains longer distances between branch points and/or an increase in intermediate material. This is in agreement with the lower gelatinization values obtained by DSC which suggested an increase in intermediate material due to an alteration in elongation/branching ratio.

Starch isolated from tubers of lines transformed with pMON17419 was analyzed for amylose content by the method of Williams, et al. (1970) *Cereal Chemistry*, 47(7): 411–420, with the following minor modifications. Exactly 100 mg of starch was dispersed in 50 ml of 0.5N KOH. The starch was added with rapid stirring with a magnetic stir bar in order to prevent clumping during gelatinization. Exactly 10 ml of the starch-KOH solution was transferred in duplicate to 100 ml volumetric flasks and diluted to 100 ml with water. Exactly 20 ml of the diluted starch solution was transferred to a new 100 ml volumetric flask and 10 ml of 0.1N HCl was added, followed by 1.0 ml of iodine reagent B. The volume was diluted to 100 ml and after five minutes the absorbance was measured at 625 nm. A standard curve was constructed by combining different volumes (totalling 10 ml) of stock solutions of potato amylose (100 mg/50 ml KOH) and potato amylopectin (100 mg/50 ml KOH) and diluting to 100 ml with water.

Duplicate analysis of starch from control (nontransformed) tubers contained approximately 23.6% amylose, while starch from pMON17419 lines 6, 12, 14, 21, 30 consisted of 31.0, 25.5, 31.3, 28.1, and 27.6% amylose, respectively. While amylose has a high affinity for iodine, intermediate material and abnormal amylopectin that contains long branch chains each possess high degrees of iodine binding capacity. Thus some of the increase in percent amylose may be attributable to longer distances between certain amylopectin branch points and/or an increase in intermediate material.

The results on the amylose content agree with the HPAEC and the DSC results which showed that starch from pMON17419-lines 6, 21, and 30 had longer distances between branch points. In addition, the increase in amylose content correlates with the altered granule morphology of starch from pMON17419 lines. The irregular, angular, cylindrical shape of the starch from the pMON17419 lines resembles the granule morphology of amylose extender starch from maize, which also has elevated levels of amylose and intermediate material. (Jane, J., et al., 1994, *Starch/Stärke* 46:121–129; Katz, F., et al., 1993, *Carb. Polymers* 21:133–136.)

Expression in Monocots

Using methods known to those in the art, a gene for an isoamylase may be stably transformed into a monocot cell and plants regenerated therefrom. See for example, U.S. Ser. No. 08/275,929 (Armstrong et al.) which corresponds to EP 586 355 A for methods of transforming and regenerating corn. To test the capability of the iam gene to be expressed in corn and other monocots, the following experiments were performed.

The CTP1-iam fusion was isolated as a BglII-EcoRI fragment from pMON17411 and subcloned into the BamHI- EcoRI sites of a pUC-based vector to give pMON17431. The CTP-iam fragment in pMON17431 was 3' to the constitutive CaMV 35S promoter and HSP70 intron, and 5' to the NOS3' transcriptional terminator (i.e., E35S/HSP70/CTP1-iam/NOS3'). A second vector, pMON17482, was similarly prepared but placed the CTP-iam fragment behind the glutelin 1 promoter in order to obtain expression in the endosperm of the corn kernel following stable transformation of regenerable corn tissues.

pMON17431 and empty control vector were purified from *E. coli* and electroporated in duplicate (100 μg DNA each) into protoplasts prepared from corn leaves. Approximately 24 h later, fractions from the electroporated cells were disrupted by sonication in 100 mM sodium phosphate, pH 6.5, and analyzed by western blot. Transient isoamylase expression in corn leaf protoplasts was estimated at 0.1% of total extracted protein.

pMON17431 was also cotransformed with the plasmid EC9 (described by Fromm et al., *Biotechnology* 8:833–839, 1990) into Black Mexican Sweet (BMS) corn callus tissue by particle gun bombardment. pEC9 contains the maize mutated ALS cDNA which confers chlorsulfuron resistance and is driven by the E35S promoter. Protein was isolated from chlorsulfuron resistant callus tissue by grinding tissue in 2% SDS, 15% glycerol, 75 mM Tris, pH 7.4, and analyzed by western blot. Isoamylase expression in BMS callus tissue was estimated at 0.025–0.05% of total extracted protein.

The CTP1-iam/NOS3' cassette was isolated as a BglII-NotI fragment from pMON17411, and subcloned into the BamHI-NotI sites of another pUC-based vector give pMON17482. The CTP-iam/NOS3' fragment in pMON17482 was 3' to the endosperm-specific rice glutelin promoter (P-osgt1) and HSP70 intron (i.e., P-osgt1/HSP70/CTP1-iam/NOS3'). Approximately 1 mg pMON17482 was purified from two liters of *E. coli* using cesium chloride density gradient centrifugation. Supercoiled plasmid DNA was used to transform corn cells by particle gun bombardment (see, e.g., EP 586 355 A, Armstrong et al.). Individual corn seed from $R_0$ plants were ground to a fine powder on liquid nitrogen. Protein was extracted from the powder by vortexing in 0.1 ml of 100 mM Tris, 10 mM EDTA, 35 mM KCl, 20% glycerol, pH 7.5, and analyzed by Western blot. Isoamylase expression in the endosperm of mature kernels was detected in five of eighteen transformed lines. The line with the highest expression of the enzyme contained isoamylase at slightly higher than 0.2% of the total extractable protein. Structural modification of the starch would be expected from expression of the enzyme in this range.

Similarly, an isoamylase gene may be transformed into wheat using known methods, such as that of Vasil et al., U.S. Pat. No. 5,405,765, incorporated herein by reference. Promoters which would be useful in expression of an isoamylase gene such as iam are discussed above. The HSP70 intron would also be used in vectors for wheat transformation.

From the foregoing, it will be seen that this invention is one well adapted to attain all the ends and objects hereinabove set forth together with advantages which are obvious and which are inherent to the invention. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

All publications and patents mentioned in this specification are herein incorporated by reference as if each individual publication or patent was specifically and individually stated to be incorporated by reference.

We claim:
1. An isolated DNA molecule which encodes the protein of SEQ ID NO:2.
2. An isolated DNA molecule of SEQ ID NO:10.
3. A transformed cell comprising a heterologous DNA sequence encoding a polypeptide having the sequence of

SEQ ID NO:11, wherein said cell is selected from *E. coli*, Bacillus sp., and yeast.

4. A DNA construct comprising operatively linked in the 5' to 3' direction:
   a) a promoter which functions to cause the production of an RNA sequence; and
   b) the structural coding sequence of SEQ ID NO:10;
wherein said promoter is heterologous to said structural coding sequence.

5. A method of producing an isoamylase comprising the steps of fermenting a culture of organisms containing the DNA construct of claim 4 and extracting isoamylase therefrom.

6. A DNA construct comprising operatively linked in the 5' to 3' direction:
   a) a promoter which functions in selected starch-producing plant cells to cause the production of an RNA sequence;
   b) a structural coding sequence that encodes for an isoamylase, wherein
      i) said isoamylase has a pH optimum of 5–8; and
      ii) said structural coding sequence hybridizes to the nucleic acid sequence of SEQ ID NO:4, or the complement thereof, under stringent hybridization conditions; and
   c) a 3' non-translated region which functions in said plant cells to cause the addition of polyadenylate nucleotides to the 3' end of the RNA sequence;
wherein said promoter is heterologous with respect to the structural coding sequence.

7. The DNA construct of claim 6 wherein said structural coding sequence further comprises a plastid targeting sequence.

8. The DNA construct of claim 7 wherein said plastid targeting sequence is the CTP-1 plastid targeting sequence SEQ ID NO:7.

9. The DNA construct of claim 6 wherein said isoamylase is SEQ ID NO:11.

10. A transformed plant cell comprising a DNA construct comprising operatively linked in the 5' to 3' direction:
    a) a promoter which functions in selected starch-producing plant cells to cause the production of an RNA sequence;
    b) a structural coding sequence that encodes for an isoamylase, wherein
       i) said isoamylase has a pH optimum of 5–8; and
       ii) said structural coding sequence hybridizes to the nucleic acid sequence of SEQ ID NO:4, or the complement thereof, under stringent hybridization conditions; and
    c) a 3' non-translated region which functions in said plant cells to cause the addition of polyadenylate nucleotides to the 3' end of the RNA sequence;
wherein said promoter is heterologous with respect to the structural coding sequence.

11. The transformed plant cell of claim 10 wherein said structural coding sequence further comprises a plastid targeting sequence.

12. The transformed plant cell of claim 11 wherein said plastid targeting sequence is the CTP-1 plastid targeting sequence SEQ ID NO:7.

13. The transformed plant cell of claim 12 wherein said isoamylase is SEQ ID NO:11.

14. The transformed plant cell of claim 13 wherein said isoamylase is encoded by SEQ ID NO:10.

15. The transformed plant cell of claim 10 wherein said plant cell is from potato, corn, wheat, barley, sweet potato, cassava, or rice.

16. The transformed plant cell of claim 10 further stably transformed with a foreign ADPglucose pyrophosphorylase gene.

17. A method of producing starch having a modified structure comprising
    a) transforming plant cells to contain a DNA construct comprising operatively liked in the 5' to 3' direction:
       i) a promoter which functions in selected starch-producing plant cells to cause the production of an RNA sequence;
       ii) a structural coding sequence that encodes for an isoamylase, wherein
          A) said isoamylase has a pH optimum of 5–8; and
          B) said structural coding sequence hybridizes to the nucleic acid sequence of SEQ ID NO:4, or the complement thereof, under stringent hybridization conditions; and
       iii) a 3' non-translated region which functions is said plant cells to cause the addition of polyadenylate nucleotides to the 3' end of the RNA sequence;
    wherein said promoter is heterologous with respect to the structural coding sequence;
    b) regenerating whole plants;
    c) multiplying said plants;
    d) harvesting plant materials; and
    e) extracting the starch therefrom.

18. The method of claim 17 wherein said structural coding sequence further comprises a plastid targeting sequence.

19. The method of claim 18 wherein said structural coding sequence comprises the CTP-1 plastid targeting sequence SEQ ID NO:7.

20. The method of claim 19 wherein said isoamylase is SEQ ID NO:11.

21. The method of claim 20 wherein said isoamylase is encoded by SEQ ID NO:10.

22. The method of claim 21 wherein said plant cell is from potato, corn, wheat, barley, sweet potato, cassava, or rice.

23. The method of claim 17 wherein said plant cells further comprise a stably transformed, foreign ADPglucose pyrophosphorylase gene.

24. A plant comprising transformed plant cells of claim 10 and containing structurally modified starch.

25. The plant of claim 24 wherein said plant is potato, corn, wheat, barley, sweet potato, cassava, or rice.

26. The plant of claim 24 wherein said structurally modified starch comprises a higher ratio of amylose to amylopectin.

27. The DNA construct of claim 6 wherein said structural coding sequence is from Flavobacterium sp.

28. The transformed plant cell of claim 10 wherein said structural coding sequence is from Flavobacterium sp.

* * * * *

UNITED STATES PATENT AND TRADEMARK OFFICE
CERTIFICATE OF CORRECTION

PATENT NO. : 5,750,876
DATED : MAY 12, 1998
INVENTOR(S) : Gerard Francis Barry/Ganesh Murthy Kishore/Bradley Martin Krohn It is certified that error appears in the above-identified patent and that said Letters Patent is hereby corrected as shown below:

In claim 3, line 2, "Bacillus" should read --*Bacillus*--.

In claim 17iii), line 26, "is" should read --in--.

In claim 27, line 58, "Flavobacterium" should read --*Flavobacterium*--.

In claim 28, line 60, "Flavobacterium" should read --*Flavobacterium*--.

Signed and Sealed this

Eighth Day of September, 1998

Attest:

BRUCE LEHMAN

Attesting Officer

Commissioner of Patents and Trademarks